(12) United States Patent
Schriver et al.

(10) Patent No.: US 10,441,775 B2
(45) Date of Patent: Oct. 15, 2019

(54) FLUID PATH SET BOLUS CONTROL DEVICE

(71) Applicant: BAYER MEDICAL CARE INC., Indianola, PA (US)

(72) Inventors: Ralph H. Schriver, Tarentum, PA (US); James A. Dedig, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 61 days.

(21) Appl. No.: 14/888,298

(22) PCT Filed: Apr. 29, 2014

(86) PCT No.: PCT/US2014/035892
§ 371 (c)(1),
(2) Date: Oct. 30, 2015

(87) PCT Pub. No.: WO2014/179326
PCT Pub. Date: Nov. 6, 2014

(65) Prior Publication Data
US 2016/0058995 A1 Mar. 3, 2016

Related U.S. Application Data

(60) Provisional application No. 61/818,056, filed on May 1, 2013.

(51) Int. Cl.
*A61M 39/24* (2006.01)
*A61M 5/168* (2006.01)
(Continued)

(52) U.S. Cl.
CPC ........ *A61M 39/24* (2013.01); *A61M 5/16827* (2013.01); *A61M 5/14216* (2013.01);
(Continued)

(58) Field of Classification Search
CPC ... F16K 15/18; A61M 39/24; A61M 5/16827; A61M 2039/1077; A61M 2039/226;
(Continued)

(56) References Cited

U.S. PATENT DOCUMENTS 3,889,710 A 6/1975 Brost
4,550,749 A 11/1985 Krikorian
(Continued)

FOREIGN PATENT DOCUMENTS

EP 1582787 A2 10/2005
JP 2002310132 A 10/2002
(Continued)

OTHER PUBLICATIONS

The International Preliminary Report dated Nov. 12, 2015 from corresponding PCT Application No. PCT/US2014/035892.
(Continued)

*Primary Examiner* — Kevin C Sirmons
*Assistant Examiner* — Tezita Z Watts
(74) *Attorney, Agent, or Firm* — David Schramm; Joseph L. Kent; James R. Stevenson

(57) ABSTRACT

A bolus control device for use with an injection device includes a valve body having a proximal end opposite a distal end. The valve body defines a fluid channel therethrough to allow a passage of medical fluid from the proximal end to the distal end. A connector at the proximal end and is configured for connecting to a fluid inlet line. A connector subassembly at the distal end and is configured for connecting to a fluid outlet line. A compressible check valve is disposed within the fluid channel, such that the compressible check valve is adjustable to control a cracking pressure at which the compressible check valve closes.

19 Claims, 17 Drawing Sheets

(51) Int. Cl.
 *A61M 5/142* (2006.01)
 *A61M 39/10* (2006.01)
 *A61M 39/22* (2006.01)
(52) U.S. Cl.
 CPC .............. *A61M 2039/1077* (2013.01); *A61M 2039/226* (2013.01); *A61M 2039/242* (2013.01); *A61M 2039/2466* (2013.01)
(58) Field of Classification Search
 CPC .... A61M 2039/242; A61M 2039/2466; A61M 5/14216
 See application file for complete search history.

(56) References Cited

U.S. PATENT DOCUMENTS

| | | | | |
|---|---|---|---|---|
| 4,919,167 | A * | 4/1990 | Manska | A61M 39/24 |
| | | | | 137/512 |
| 5,289,849 | A * | 3/1994 | Paradis | A61M 39/04 |
| | | | | 137/606 |
| 5,983,920 | A | 11/1999 | Gapinski et al. | |
| 5,989,240 | A * | 11/1999 | Strowe | A61M 39/12 |
| | | | | 285/340 |
| 6,390,130 | B1 * | 5/2002 | Guala | A61M 39/24 |
| | | | | 137/859 |
| 6,706,022 | B1 | 3/2004 | Leinsing | |
| 7,094,216 | B2 | 8/2006 | Trombley et al. | |
| 7,556,619 | B2 | 7/2009 | Spohn et al. | |
| 7,824,393 | B2 * | 11/2010 | Fangrow | A61M 39/26 |
| | | | | 604/533 |
| 8,147,464 | B2 | 4/2012 | Spohn et al. | |
| 8,337,456 | B2 | 12/2012 | Schriver et al. | |
| 9,259,527 | B2 | 2/2016 | Spohn et al. | |
| 2004/0006330 | A1 * | 1/2004 | Fangrow, Jr. | A61M 39/02 |
| | | | | 604/533 |
| 2004/0064041 | A1 | 4/2004 | Lazzaro et al. | |
| 2005/0113754 | A1 | 5/2005 | Cowan et al. | |
| 2005/0217731 | A1 * | 10/2005 | Abe | F16K 17/06 |
| | | | | 137/540 |
| 2007/0219480 | A1 * | 9/2007 | Kamen | G05D 7/0647 |
| | | | | 604/20 |
| 2008/0058720 | A1 * | 3/2008 | Spohn | A61M 5/007 |
| | | | | 604/140 |
| 2008/0086087 | A1 | 4/2008 | Spohn et al. | |
| 2012/0123257 | A1 | 5/2012 | Stokes, Jr. et al. | |
| 2014/0000730 | A1 * | 1/2014 | Nguyen | F16K 15/025 |
| | | | | 137/511 |

FOREIGN PATENT DOCUMENTS

| | | |
|---|---|---|
| JP | 6266064 B2 | 1/2018 |
| WO | 0107102 A2 | 2/2001 |
| WO | 2007083599 A1 | 7/2007 |
| WO | 2010051205 A2 | 5/2010 |
| WO | 2012155035 A1 | 11/2012 |

OTHER PUBLICATIONS

The International Search Report and Written Opinion dated Oct. 3, 2014 from corresponding PCT Application No. PCT/US2014/035892.

"Extended European Search Report from EP Application No. 14791318", dated Jan. 2, 2017.

* cited by examiner

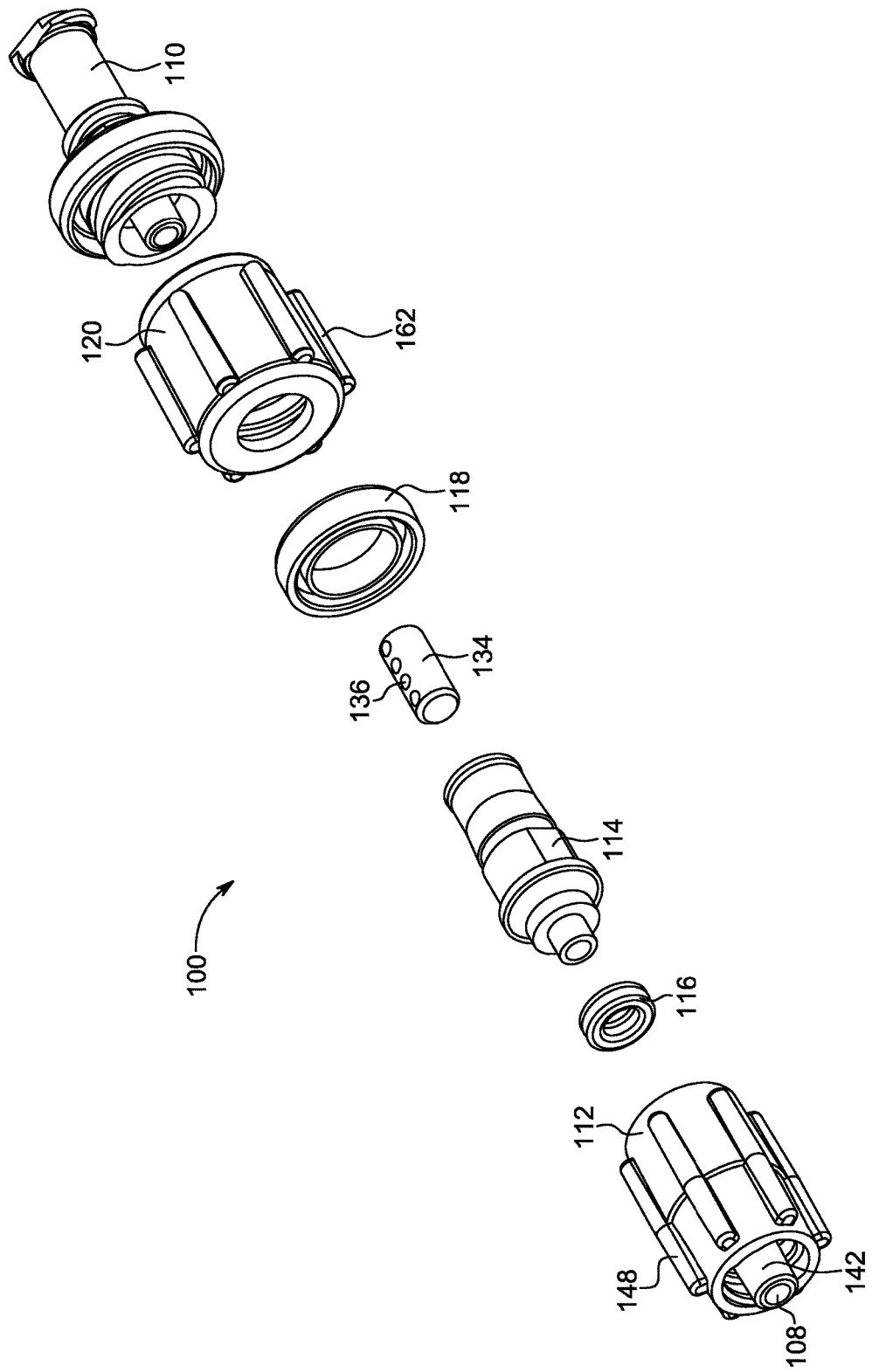

FLUID PATH SET BOLUS CONTROL DEVICE

CROSS-REFERENCE TO RELATED APPLICATIONS

This application is a U.S. national stage filing under 35 U.S.C. § 371 of International Application No. PCT/US2014/035892, filed Apr. 29, 2014, which claims priority to U.S. Provisional Patent Application No. 61/818,056, filed on May 1, 2013 and entitled "Fluid Path Set Bolus Control Device", the disclosure of which is hereby incorporated by reference in its entirety.

BACKGROUND OF THE DISCLOSURE

Field of the Disclosure

The present disclosure is directed to medical fluid delivery applications and, particularly, to a fluid path set bolus control device.

Description of Related Art

In many medical diagnostic and therapeutic procedures, a medical practitioner, such as a physician, injects a patient with a medical fluid. In recent years, a number of injector-actuated syringes and powered injectors for pressurized injection of fluids, such as contrast solution (often referred to simply as "contrast"), have been developed for use in procedures such as angiography, computed tomography (CT), ultrasound, and NMR/MRI. In general, these powered injectors are designed to deliver a preset amount of contrast at a preset flow rate.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path may also include, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, such as stopcocks. The operator of the manual contrast injection mechanism controls the syringe and each of the valves to draw saline or contrast into the syringe and to inject the contrast or saline into the patient through the catheter connection.

Automatic contrast injection mechanisms typically include a syringe connected to one or more powered injectors having, for example, a powered linear actuator. Typically, an operator enters settings into an electronic control system of the powered injector for a fixed volume of contrast and/or saline, and a fixed rate of injection for each. Automatic contrast injection mechanisms provide improved control over manual apparatus where successful use of such manual devices is dependent on the skill of the medical practitioner operating the device. As in a manual system, the fluid path from the automatic contrast injection mechanism to the patient includes, for example, a source of contrast, a source of flushing fluid, typically saline, and a pressure transducer to measure patient blood pressure. The source of contrast is connected to the fluid path via a valve, for example, a three-way stopcock. The source of saline and the pressure transducer may also be connected to the fluid path via additional valves, such as stopcocks.

The injected contrast is delivered to a desired site in a patient's body through the catheter inserted into the patient's body, such as the patient's groin area. A dose of contrast is referred to as a bolus. Once the bolus of contrast is delivered to the desired site, that area is imaged using a conventional imaging technique, such as angiography imagining or scanning. The contrast becomes clearly visible against the background of the surrounding tissue.

Due to high injection pressure in contrast injection mechanisms, which typically may reach 1200 psi in automatic contrast injection mechanisms, there may be an expansion of system components such that there may be a quantity of contrast solution in excess of the desired quantity selected for the injection procedure. Such increase in the quantity of the contrast occurs due to system capacitance. Total system capacitance represents the amount of suppressed fluid that is captured in the swelling of the system components due to pressure. Total system capacitance is inherent to each automatic contrast injection mechanism and depends on a plurality of factors, including injector construction, mechanical properties of materials used to construct the syringe, piston, pressure jacket surrounding the syringe, inlet and outlet fluid lines, size and sidewall thickness of the syringe, etc. After the injection procedure is completed, the system returns to its original state by relieving the excess quantity of fluid, which is often manifested as dribbling of the contrast from the catheter tip. This increases the quantity of the contrast delivered to the injection site, resulting in an inaccurate bolus and image irregularities.

SUMMARY OF THE DISCLOSURE

While manual and automated injectors are known in the medical field, improved fluid delivery systems having a bolus control device to control an excess dribbling of contrast continue to be in demand in the medical field.

In view of the disadvantages of the existing manual and automated contrast injection mechanisms, there is a need in the art for a bolus control device adapted for use with an existing fluid path set. There is an additional need for a bolus control device that prevents dribbling of excess contrast from the catheter tip after an injection. A further need exists in the art for a bolus control device having one or more elements adapted to provide an adjustable control of cracking pressure at which the bolus control device prevents dribbling of excess contrast from the catheter tip after an injection.

In accordance with one embodiment, a bolus control device for use with an injection device may include a valve body having a proximal end opposite a distal end, the valve body defining a fluid channel therethrough. The bolus control device may further include a first connector at the proximal end configured for connecting to a fluid inlet line and a second connector at the distal end configured for connecting to a fluid outlet line. A compressible check valve may be disposed within the fluid channel and compressible in response to fluid pressure within the fluid channel. The compressible check valve may be adjustable to control a cracking pressure at which the compressible check valve opens to allow fluid flow through the fluid channel.

The bolus control device may further include an intermediate element disposed between the first connector and the second connector, wherein the fluid channel extends through an interior cavity of the intermediate element. The compressible check valve may be disposed within the interior cavity of the intermediate element such that the fluid channel extends radially around the compressible check valve. The compressible check valve may be disposed between a distal end of the first connector and a distal end of the intermediate element such that the compressible check valve is compressible under fluid pressure in a distal direction from the distal end of the first connector toward the distal end of the intermediate element. An axial position of the first connector may be adjustable relative to the intermediate element to adjust a compression of the compressible check valve between a distal end of the first connector and a distal end of the intermediate element.

A collar may be provided to extend around at least a portion of the first connector and the intermediate element. The collar may be rotatable relative to the first connector to adjust the axial position of the first connector relative to the intermediate element. The collar may be connected to the first connector by a threaded connection. Rotation of the collar relative to the first connector may adjust a compression of the compressible check valve.

In accordance with another embodiment, a fluid path set for use with an injection device may include a fluid inlet line, a fluid outlet line, and a bolus control device disposed between the fluid inlet line and the fluid outlet line. The bolus control device may include a valve body having a proximal end opposite a distal end, the valve body defining a fluid channel therethrough. The bolus control device may further include a first connector at the proximal end configured for connecting to the fluid inlet line and a second connector at the distal end configured for connecting to the fluid outlet line. A compressible check valve may be disposed within the fluid channel and compressible in response to fluid pressure within the fluid channel. The compressible check valve may be adjustable to control a cracking pressure at which the compressible check valve opens to allow fluid flow through the fluid channel.

An intermediate element may be disposed between the first connector and the second connector, wherein the fluid channel extends through an interior cavity of the intermediate element. The first connector may be connected to the fluid inlet line by a threaded connection. Similarly, the second connector may be connected to the fluid outlet line by a threaded connection. The fluid inlet line may be configured for connecting to a fluid injection device. The fluid outlet line may be configured for connecting to a catheter for delivering fluid to a patient.

In accordance with another embodiment, a bolus control device for use with an injection device may include a valve body having a proximal end opposite a distal end, the valve body defining a fluid channel therethrough. The bolus control device may further include a first connector at the proximal end configured for connecting to the fluid inlet line and a second connector at the distal end configured for connecting to the fluid outlet line. A compressible check valve may be disposed within the fluid channel and compressible in response to fluid pressure within the fluid channel. The bolus control device may further include an adjustment mechanism for adjusting a compression of the compressible check valve against the first connector to control a cracking pressure at which the compressible check valve opens to allow fluid flow through the fluid channel.

The adjustment mechanism may include a housing with a cavity configured to receive a valve stem having an eccentric cam element. The compressible check valve may be disposed between a distal end of the first connector and the eccentric cam element such that the compressible check valve is compressible under fluid pressure in a distal direction from the distal end of the first connector toward the eccentric cam element. The eccentric cam element may be rotatable within the housing of the adjustment mechanism. Rotation of the eccentric cam element adjusts the compression of the compressible check valve against the first connector to control a cracking pressure at which the compressible check valve opens to allow fluid flow through the fluid channel. An intermediate element may be disposed between the second connector and the housing of the adjustment mechanism, wherein the fluid channel extends through an interior cavity of the intermediate element.

These and other features and characteristics of the fluid path set bolus control device, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

BRIEF DESCRIPTION OF THE DRAWINGS

FIG. 4C is an exploded view of the bolus control device shown in FIG. 4A.

DESCRIPTION OF THE PREFERRED EMBODIMENTS

Figure 1:
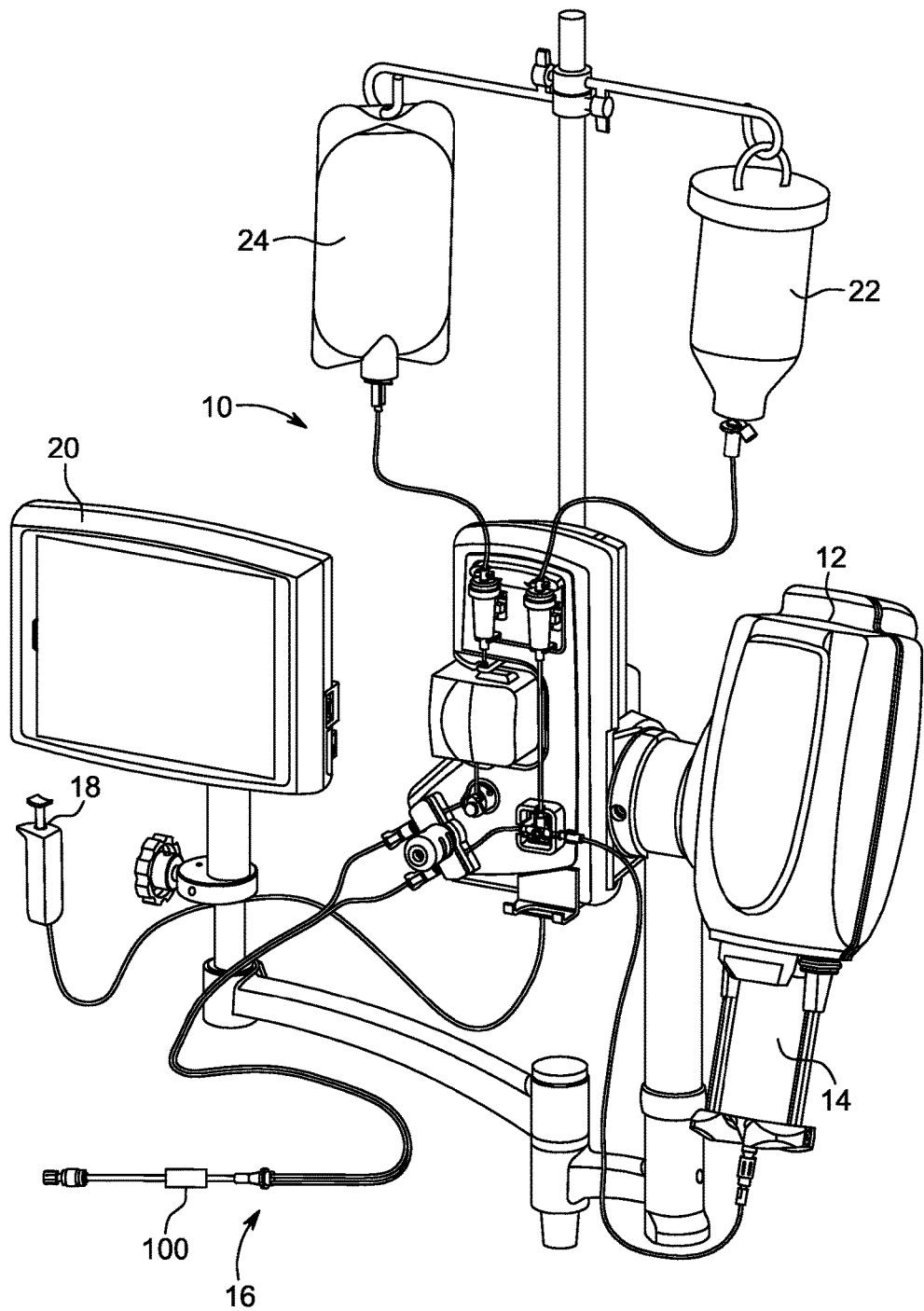
FIG. 1 is a perspective view of a fluid delivery system according to one embodiment.

For purposes of the description hereinafter, spatial orientation terms shall relate to the referenced embodiment as it is oriented in the drawing figures. However, it is to be understood that the various embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

Referring to the drawings in which like reference characters refer to like parts throughout the several views thereof, the present disclosure is generally directed to a bolus control device adapted for connection to a fluid path set used in an injection system.

FIG. 1 is a perspective view of a fluid delivery system 10 having a fluid path set bolus control device 100 according to one embodiment. The fluid delivery system 10 is adapted for delivering fluids to a patient during a medical injection procedure. For example, the fluid delivery system 10 may be used during an angiographic procedure to inject a contrast solution and/or a common flushing agent, such as saline, into the body of a patient. An example of such a fluid injection or delivery system is disclosed in U.S. patent application Ser. No. 09/982,518, filed on Oct. 18, 2001, now issued as U.S. Pat. No. 7,094,216 on Aug. 22, 2006 (hereinafter "the '216 patent"), and assigned to the assignee of the present application, the disclosure of which is incorporated herein by reference in its entirety. Additional examples of fluid delivery systems are disclosed in the following references: U.S. patent application Ser. No. 10/825,866, filed on Apr. 16, 2004, now issued U.S. Pat. No. 7,556,619 on Jul. 7, 2009 (hereinafter "the '619 patent"); U.S. patent application Ser. No. 12/437,011, filed May 7, 2009, now issued U.S. Pat. No. 8,337,456 to Schriver et al. on Dec. 25, 2012; U.S. patent application Ser. No. 12/476,513, filed Jun. 2, 2009, now issued U.S. Pat. No. 8,147,464 to Spohn et al. on Apr. 3, 2012; and U.S. patent application Ser. No. 11/004,670, filed on Dec. 3, 2004 now published as U.S. 2008/0086087 on Apr. 10, 2008, each of which are assigned to the assignee of the present application and the disclosures of which are incorporated herein by reference in their entireties. The bolus control device 100 is generally adapted to interface with one or more components of the fluid delivery system 10 to aid in the prevention of excess fluid leakage after an injection procedure is completed, as will be described hereinafter.

The fluid delivery system 10 generally includes a powered fluid injector 12 that is adapted to support and actuate a syringe 14 storing a first injection fluid 22 for injection to a patient during a medical procedure, such as an angiographic procedure. The fluid delivery system 10 further includes a second injection fluid 24 that may be mixed with the first injection fluid 22 prior to being delivered to a patient. The injector 12 is generally used to supply the first and second injection fluids 22, 24 under pressure to the fluid path set 16 and, ultimately, the patient. The injector 12 may be controlled by a hand controller 18 to supply the first and second injection fluids 22, 24 at discrete and preselected flow rates based on the physical inputs to the hand controller 18.

The following operational discussion of the bolus control device 100 will be with exemplary reference to an angiographic procedure involving the fluid delivery system 10 and how the bolus control device 100 contributes to the homogeneous mixing of the first injection fluid 22 and the second injection fluid 24 from the fluid delivery system 10. In typical angiographic procedures, the first injection fluid 22 is contrast solution and the second injection fluid 24 or flushing agent is saline. The contrast solution typically has higher viscosity and specific gravity compared to saline. One of ordinary skill in the art will appreciate that, depending on the medical procedure, various other medical fluids can be used as the first injection fluid 22 and the second injection fluid 24.

The injector 12 is operatively associated with a fluid control module 20. The fluid control module 20 may be adapted for controlling the operation of the fluid delivery system 10 by allowing the user to manually select the injection parameters, or select a pre-defined injection protocol. Alternatively, this functionality may reside with an external control unit or with the powered injector 12. In either case, the fluid control module 20 controls the injection pressure and the ratio of the first injection fluid 22 relative to the second injection fluid 24. The fluid control module 20 is generally adapted to support a fluid path set 16 that is generally adapted to fluidly connect the syringe 14 to a source of first injection fluid 22 (contrast solution). The fluid path set 16 is further connected to a source of second injection fluid 24 (saline) which is supplied to the patient via the same catheter as the contrast solution. In one embodiment, the second injection fluid 24 may be delivered by way of a second powered injector, as described in greater detail below. In another embodiment, the second injection fluid 24 may be delivered by way of a pump, such as a piston pump or a peristaltic pump. The bolus control device 100 is disposed within the fluid path set 16. The flow of contrast and saline is regulated by the fluid control module 20 which controls the various valves and flow regulating structures in the fluid path set 16 to regulate the delivery of contrast and saline to the patient based on user selected injection parameters, such as total injection volume and ratio of contrast solution and saline. The fluid path set 16 further connects the syringe 14 to a catheter (not shown) which is associated with the patient for supplying the contrast solution and saline to the patient. In one embodiment, the catheter can be connected directly to the bolus control device 100.

Figure 2:
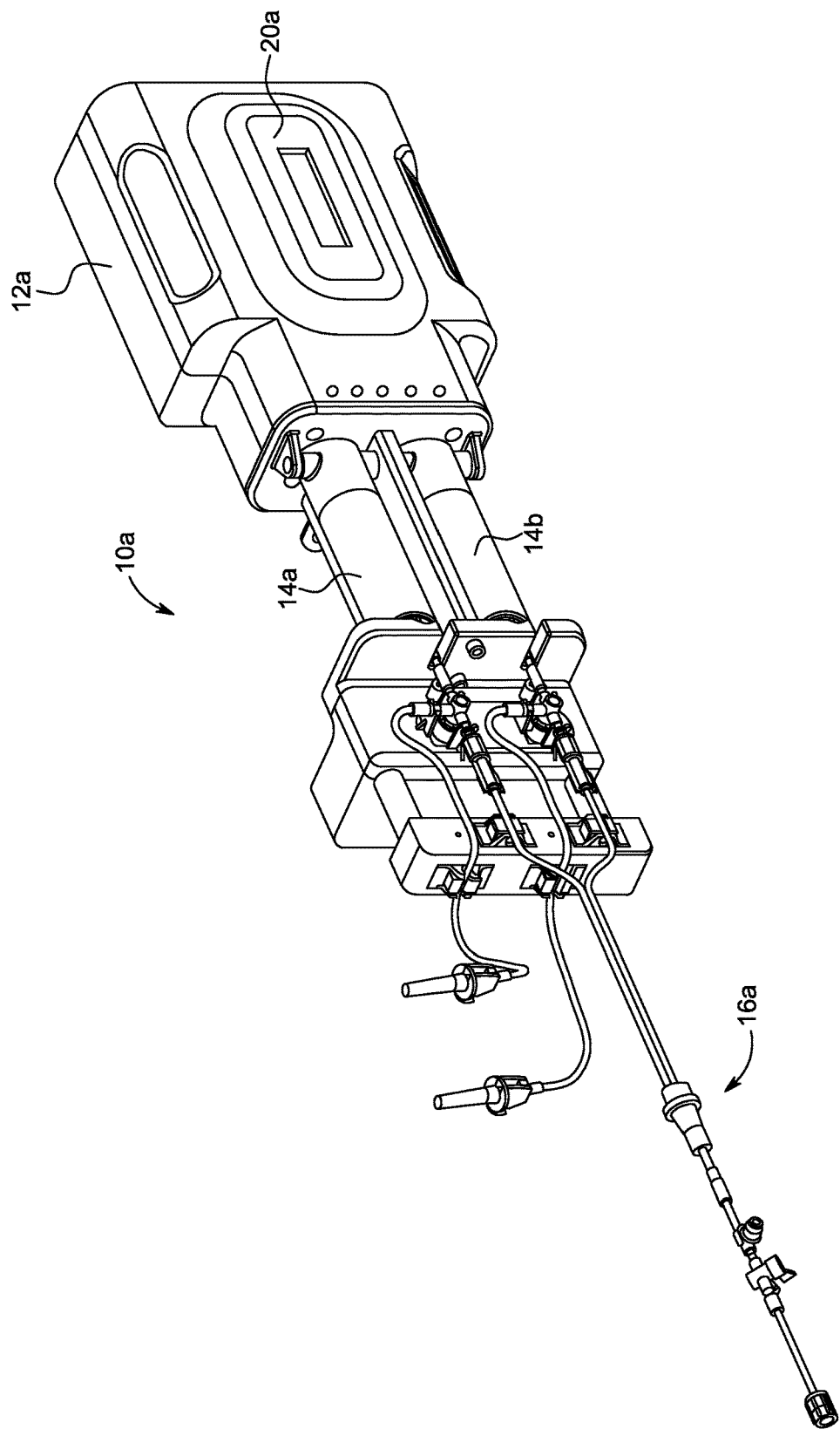
FIG. 2 is a perspective view of a fluid delivery system according to another embodiment.

FIG. 2 illustrates an alternative embodiment of a fluid delivery system 10a having a powered fluid injector 12a adapted to interface with two syringes 14a, 14b which may be fluidly connected to a source of first injection fluid 22 and a source of second injection fluid 24 or any two desired medical fluids. The injector 12a is desirably at least a dual-syringe injector, wherein two fluid delivery syringes are oriented in a side-by-side relationship and which are separately actuated by respective piston elements associated with the injector 12a. In another embodiment, the injector 12a may be a dual-pump injector, wherein two pumps, such as piston pumps and/or peristaltic pumps, are separately actuated and controlled. The fluid path set 16a may be interfaced with the injector 12a in a similar manner to that described previously in connection with the fluid delivery system 10 described with reference to FIG. 1. In particular, the injector 12a is operatively associated with a fluid control module 20a. The fluid control module 20a is generally adapted to support a fluid path set 16a that is generally adapted to fluidly connect to the first syringe 14a having a first injection fluid 22, such a contrast solution. The fluid path set 16a is further connected to the second syringe 14b having a second injection fluid 24, such as saline. The first and second syringes 14a, 14b may have a different size relative to each other. One of the first syringe 14a and the second syringe 14b is larger relative to the other of the first syringe 14a and the second syringe 14b to receive a larger volume of fluid therein. The bolus control device 100 is disposed within the fluid path set 16a. The flow of the first injection fluid 22 from the first syringe 14a and the second injection fluid 24 from the second syringe 14b is regulated by the fluid control module 20a, which controls the various valves and flow regulating structures to regulate the delivery of first and second medical fluids to the patient based on user selected injection parameters, such as total injection volume and ratio of contrast solution and saline. The fluid path set 16a further connects to a catheter (not shown) which is associated with the patient for supplying the first and second medical fluids to the patient. A suitable multi-syringe fluid injector for use with the above-described system is described in U.S. patent application Ser. No. 13/386,765, filed on Jan. 24, 2012, which published as U.S. Patent Application Publication No. 2012/0123257, and is assigned to the assignee of the present application, the disclosure of which is incorporated herein by reference in its entirety. Other relevant multi-fluid delivery systems are found in U.S. patent application Ser. No. 10/159,592, filed on May 30, 2002 (published as U.S. 2004/0064041), U.S. patent application Ser. No. 10/722,370, filed Nov. 25, 2003 (published as U.S. 2005/0113754), and International Patent Application No. PCT/US2012/037491, filed on May 11, 2012 (published as WO 2012/155035), all of which are assigned to the assignee of the present application, and the disclosures of which are incorporated herein by reference.

In yet another embodiment, a three-fluid delivery system (not shown) may be provided. Similar to power-operated fluid delivery systems described with reference to FIGS. 1-2, a three-fluid delivery system may include a first injector or pump adapted to deliver a first injection fluid 22, such as a contrast medium, a second injector or pump adapted to deliver a second injection fluid 24, such as saline, and a third injector or pump adapted to deliver a third injection fluid. A fluid path set is provided for delivering and mixing the first, second, and third injection fluids in a desired ratio prior to being delivered to a patient. An exemplary three-fluid delivery system is disclosed in FIGS. 60-62 of U.S. Patent Application Publication No. 2012/0123257 discussed above.

In another embodiment, a manually-controlled fluid delivery system (not shown) may be provided. Similar to power-operated fluid delivery systems described with reference to FIGS. 1-2, a manually-controlled fluid delivery system may include a first injector adapted to actuate a first syringe storing a first injection fluid 22, such as a contrast medium, for injection to a patient during a medical procedure. The manually-controlled fluid delivery system may also include a second injector adapted to actuate a second syringe storing a second injection fluid 24, such as saline. A fluid path set is provided for delivering and mixing the first injection fluid 22 and the second injection fluid 24 in a desired ratio prior to being delivered to a patient. An exemplary manually-controlled fluid delivery system is disclosed in U.S. patent application Ser. No. 13/755,883, filed Jan. 31, 2013, assigned to the assignee of the present application, the disclosure of which is incorporated herein by reference.

Figure 3:
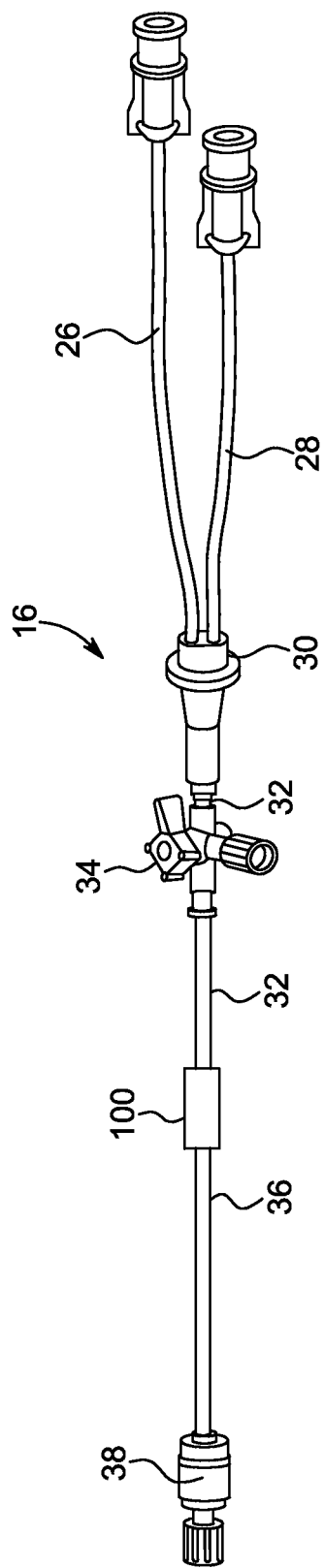
FIG. 3 is a top perspective view of a fluid path for use in a fluid delivery system.

With reference to FIG. 3, the fluid path set 16 is shown removed from the fluid delivery system 10. The fluid path set 16 includes a first fluid line 26 in fluid communication at its proximal end with the source of the first injection fluid 22 and a second fluid line 28 in fluid communication at its proximal end with the source of the second injection fluid 24. First and second fluid lines 26, 28 act as fluid conduits for delivering the first and second injection fluid 22, 24, respectively, from the source of each respective fluid. Distal ends of each of the first and second fluid lines 26, 28 are in fluid communication with a fluid connector 30 that combines the first and second fluid lines 26, 28 into a single fluid inlet line 32. One or more valves 34 may be provided within the fluid path set 16 to selectively block the passage of the first and/or second injection fluid 22, 24 through the fluid path set 16. For example, a one-way valve may be provided on the fluid inlet inline 32 to prevent the contrast and/or saline from flowing back into the fluid connector 30. In one embodiment, the one or more valves 34 may be provided directly on the bolus control device 100, which is connected to the fluid inlet line 32 at its proximal end. A fluid outlet line 36 extends from the distal end of the bolus control device 100. The distal end of the fluid outlet line 36 is desirably connected to a catheter (not shown) by a connector 38 to deliver the mixed solution of the first and second injection fluid 22, 24 to the patient. The connector 38 may be bonded to the fluid outlet line 36 by a conventional UV bonding technique. Alternatively, the connector 38 may be coupled to the fluid outlet line 36 by an over-molding technique. The connector 38 may have a luer-type connection at its distal end configured for coupling with a corresponding luer-type connection on the catheter.

Figure 4A:
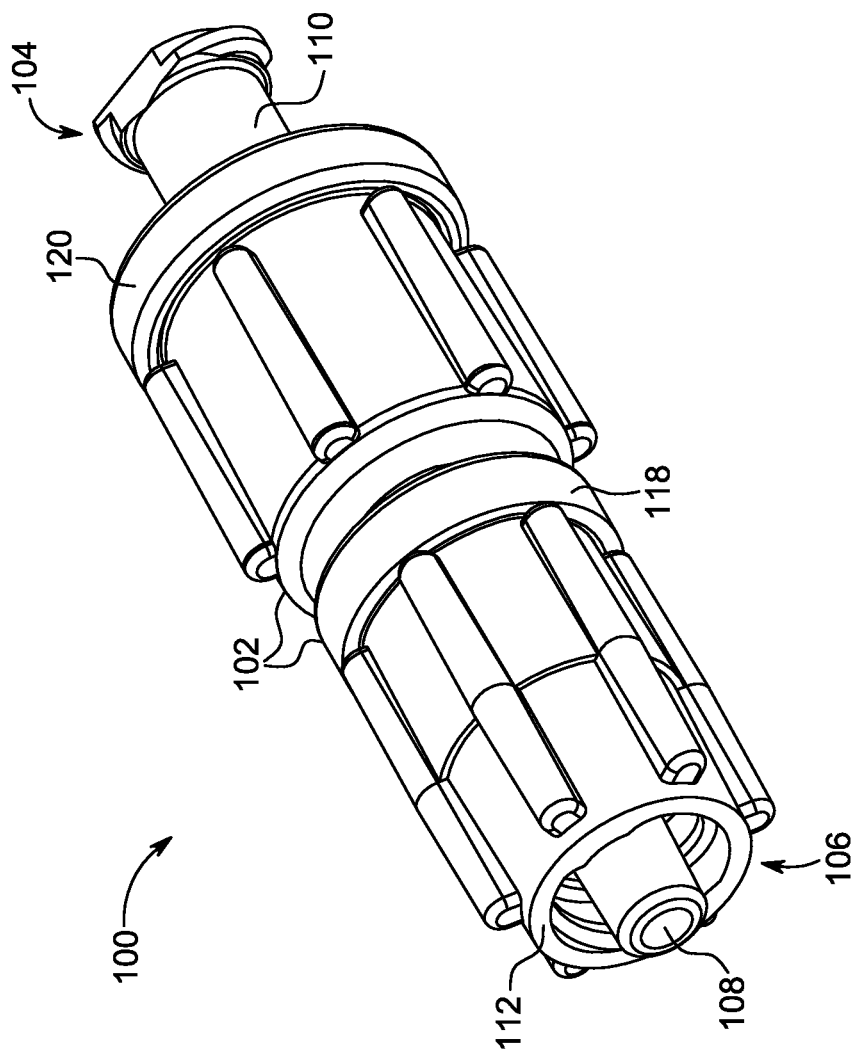
FIG. 4A is a perspective view of a bolus control device in accordance with a first embodiment.

With reference to FIG. 4A, a bolus control device 100 is shown in accordance with a first embodiment. The bolus control device 100, as described herein, is intended for connection to a fluid injection system, as will be readily apparent to those skilled in the medical art. The bolus control device 100 includes a valve body 102 having a proximal end 104 opposite a distal end 106. The valve body 102 defines a fluid channel 108 therethrough to allow a passage of a medical fluid from the proximal end 104 to the distal end 106. A first connector 110 is provided at the proximal end 104 and is configured for connecting to the fluid inlet line 32 (shown in FIG. 3). For example, the first connector 110 may be a male luer-type connector for connecting to a female end of a corresponding luer-type connector of the fluid inlet line 32 (shown in FIG. 3). A second connector 112 is provided at the distal end 106 and is configured for connecting to the fluid outlet line 36 (shown in FIG. 3), or directly to a catheter (not shown). Similar to the first connector 110, the second connector 112 may be a female luer-type connector for connecting to a male end of a corresponding luer-type connector of the fluid outlet line 36 leading to an injection site. Alternatively, the first connector 110 may be a female luer-type connector, and the second connector 112 may be a male luer-type connector. In yet another embodiment, the first and second connectors 110, 112 may be male or female luer-type connectors. One of ordinary skill in the art will appreciate that the first connector 110 and the second connector 112 may be embodied as any type of mechanical connector known in the medical arts for connecting a plurality of components in the fluid path set 16 (shown in FIG. 3).

Figure 4B:
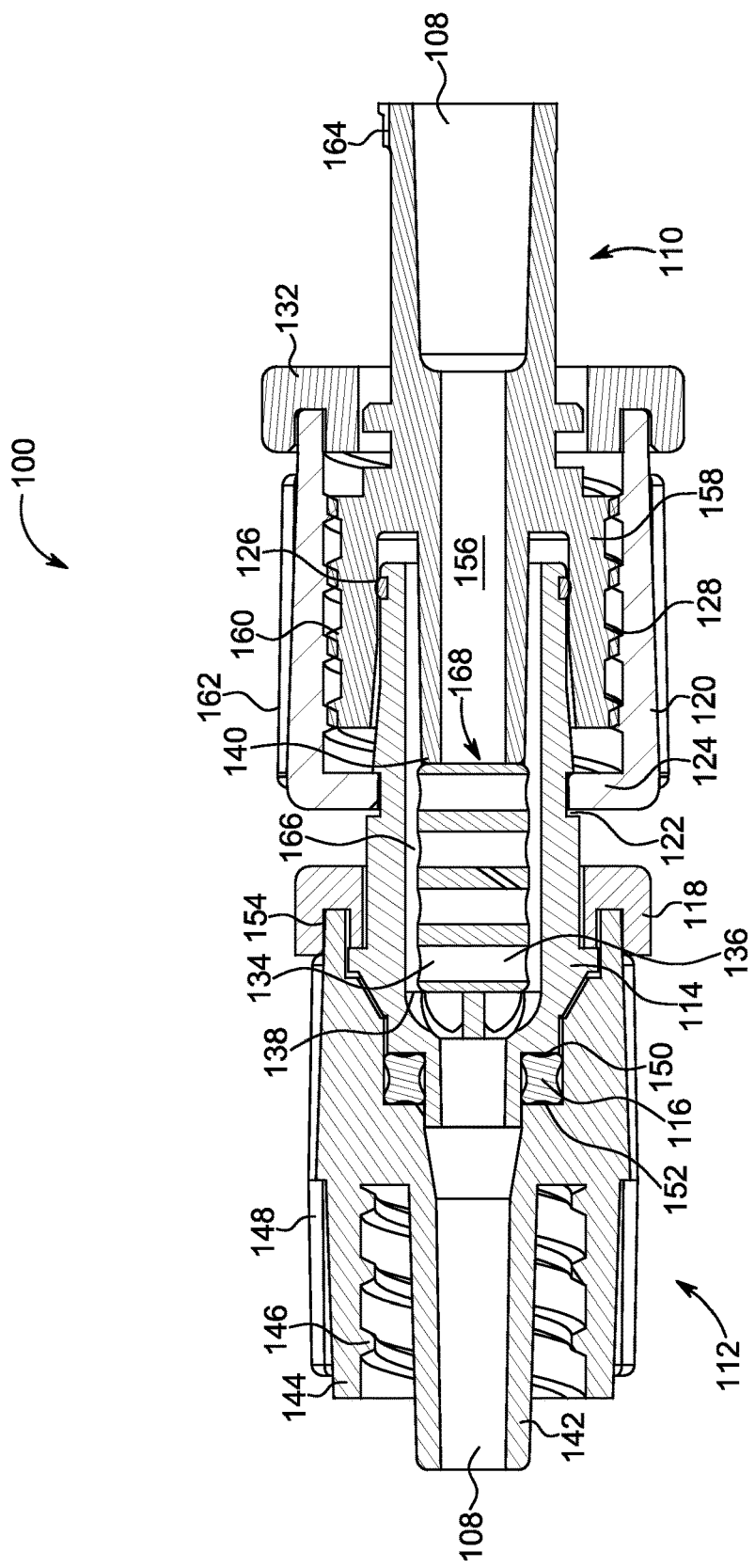
FIG. 4B is a cross-sectional view of the bolus control device shown in FIG. 4A.

With reference to FIG. 4B, the second connector 112 has a generally tubular structure with the fluid channel 108 extending along its central axis. The second connector 112 has a central lumen 142 extending along the central axis. The central lumen 142 is surrounded by an annular skirt 144 that is concentric about the central lumen 142. The annular skirt 144 has internal threads 146 configured for connecting to the fluid outlet line 36 (shown in FIG. 3). Alternatively, the annular skirt 144 may have external threads. The exterior portion of the second connector 112 has one or more protrusions 148 that extend radially outward. The protrusions 148 are configured for facilitating the handling of the bolus control device 100. For example, the protrusions 148 may provide a gripping surface that is grasped by the user to facilitate connection with the fluid outlet line 36.

With continuing reference to FIG. 4B, the second connector 112 is connected to an intermediate part 114. In one embodiment, the second connector 112 may be formed as a separate component removably or non-removably coupled with the intermediate part 114. Alternatively, the second connector 112 may be integrally formed with the intermediate part 114. The intermediate part 114 has a generally tubular structure with a distal end having a radial face 150 configured for defining a sealing interface with an annular end wall 152 on the second connector 112. A gasket 116, such as an O-ring, seals the sealing interface between the second connector 112 and the intermediate part 114. The gasket 116 is disposed between the radial face 150 of the intermediate part 114 and the annular end wall 152 of the second connector 112. The gasket 116 is desirably made from a flexible and resilient material, such as rubber, to provide a seal at the interface between the second connector 112 and the intermediate part 114.

With continuing reference to FIG. 4B, a ring 118 connects the second connector 112 and the intermediate part 114 together. The ring 118 is substantially annularly shaped and defines a connection member 154 for connecting the second connector 112 to the intermediate part 114. In one embodiment, the ring 118 non-removably connects the second connector 112 and the intermediate part 114. In another embodiment, the second connector 112 and the intermediate part 114 are removably connected together. For example, the ring 118 may be threadably connected to the second connector 112 by way of the connection member 154 such that, when fully threaded with the second connector 112, the ring 118 urges the intermediate part 114 toward the second connector 112. In this manner, the gasket 116 is compressed between the second connector 112 and the intermediate part 114 to provide a sealed interface therebetween.

With continuing reference to FIG. 4B, a sleeve 120 is secured to the intermediate part 114 by engaging a recess 122 on the intermediate part 114. The recess 122 desirably surrounds at least a portion of an outer circumference of the intermediate part 114 and is recessed radially inward relative to the surrounding portions of the intermediate part 114. The sleeve 120 includes a lip 124 that engages the recess 122 to prevent relative axial movement between the sleeve 120 and the intermediate part 114. The lip 124 extends radially inward from the body of the sleeve 120 and is shaped to be received within the recess 122. The lip 124 desirably surrounds at least a portion of an outer circumference of the sleeve 120 and protrudes radially inward relative to the surrounding portions of the sleeve 120. At least a portion of the lip 124 is received in a radial direction about the circumference of the recess 122.

Similar to the second connector 112, the first connector 110 has a generally tubular structure with the fluid channel 108 extending along its central axis. The first connector 110 has a central lumen 156 extending along the central axis. The central lumen 156 is surrounded by an annular skirt 158 that is concentric about the central lumen 156. The annular skirt 158 has external threads 160 configured for being threadably connected to the sleeve 120 such that the first connector 110 may be threadably moved relative to the intermediate part 114. The distal end of the central lumen 156 is configured for interacting with a check valve disposed with the intermediate part 114, as will be described hereinafter. The proximal end of the central lumen 156 has a luer-type connector 164 for connecting with the fluid inlet line 32 (shown in FIG. 3).

The sleeve 120 has a generally tubular structure shaped to extend around the outer circumference of the intermediate part 114 and the first connector 110. The exterior portion of the sleeve 120 has one or more protrusions 162 that extend radially outward. The protrusions 162 are configured for facilitating the handling of the bolus control device 100. For example, the protrusions 162 may provide a gripping surface that is grasped by the user to facilitate connection with the fluid inlet line 32 (shown in FIG. 3).

An interface between the first connector 110 and the intermediate part 114 is sealed by a gasket 126, such as an O-ring. In the embodiment shown in FIG. 4B, the gasket 126 is disposed radially about an outer circumference of the intermediate part 114. However, in alternate embodiments, the gasket 126 may be provided on an inner circumference of the first connector 110. One of ordinary skill in the art will appreciate that any other sealing mechanism may be used to seal the interface between the intermediate part 114 and the first connector 110.

The sleeve 120 includes threads 128 along an inner circumference thereof that correspond to the threads 160 on an outer circumference of the first connector 110. As such, the first connector 110 is movable axially relative to the sleeve 120 between the proximal and distal ends 104, 106 of the valve body 102. A cap 132 is provided at a proximal end of the sleeve 120 to prevent the first connector 110 from being completely unthreaded from the sleeve 120. While FIGS. 4A-4C show a threaded connection between the sleeve 120 and the first connector 110, any other type of mechanical connection may be used. For example, the sleeve 120 and the first connector 110 may be connected in a sliding, frictional fit connection.

Figure 5A:
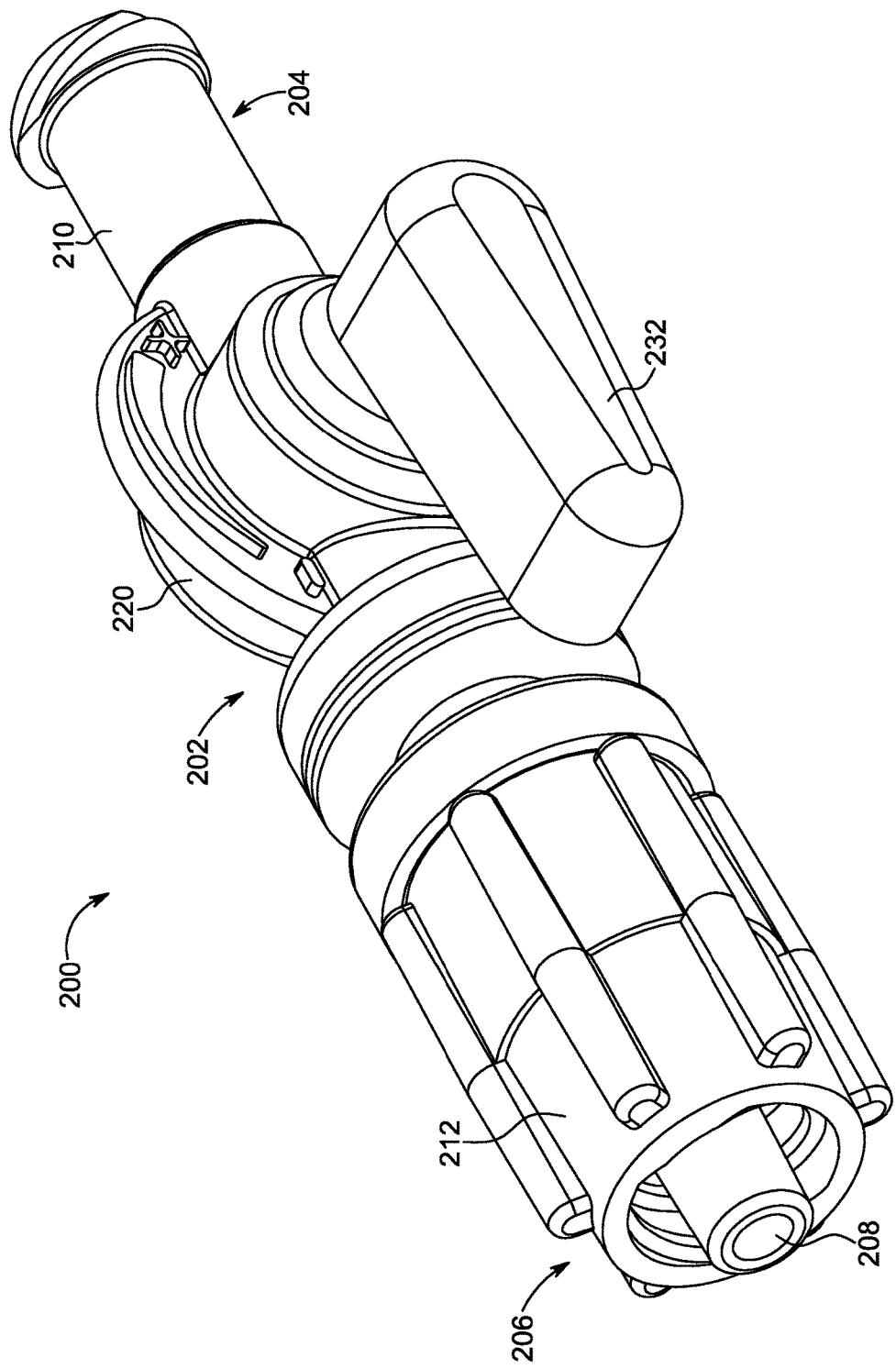
FIG. 5A is a perspective view of a bolus control device in accordance with a second embodiment.
Figure 5B:
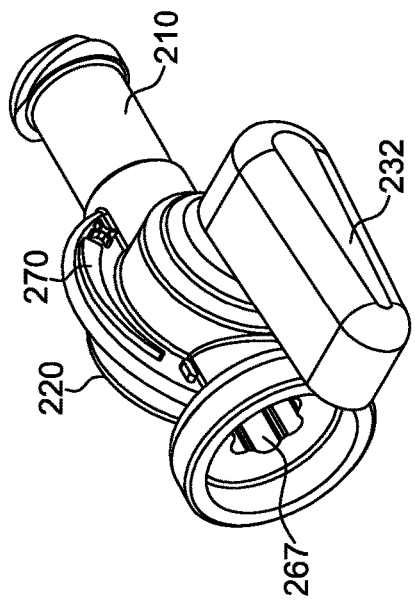
FIG. 5B is an exploded view of the bolus control device shown in FIG. 5A.
Figure 5B:
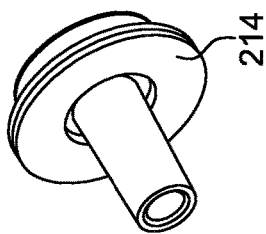
Figure 5B:
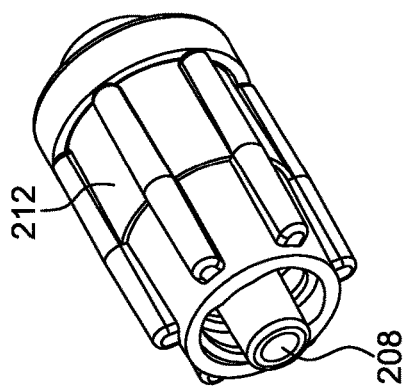
Figure 5C:
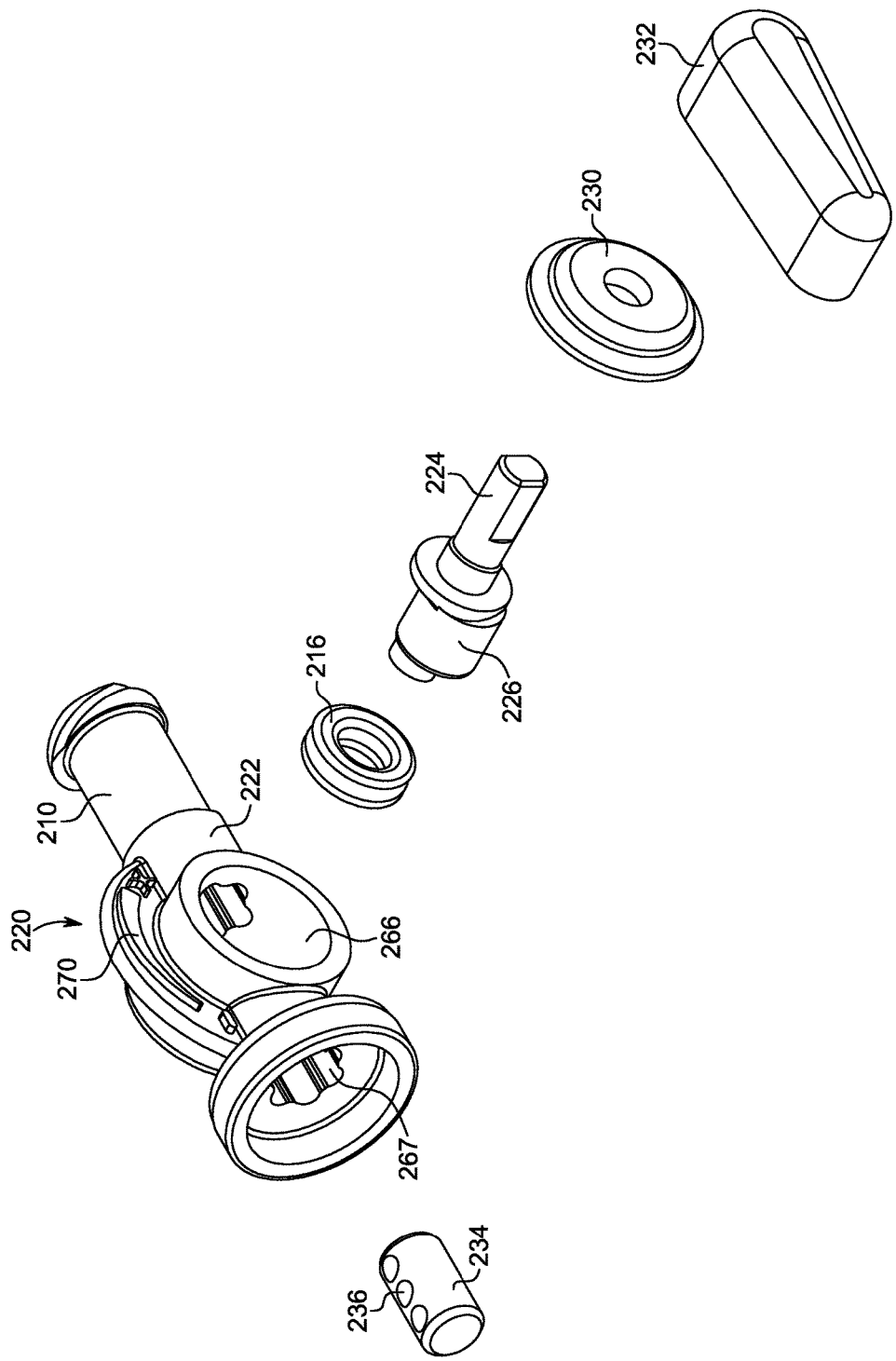
FIG. 5C is an exploded view of an adjustment mechanism of the bolus control device of FIG. 5A.

With continuing reference to FIG. 4B, a compressible check valve 134 is disposed within a cavity 166 extending through the intermediate part 114. The cavity 166 is aligned with a central axis of the bolus control device 100 such that the cavity 166 defines the portion of the fluid channel 108 extending through the intermediate part 114. The compressible check valve 134 is desirably dimensioned such that its outer diameter is slightly smaller than an inner diameter of the cavity 166 such that fluid pass around the check valve 134 and through the cavity 166. In one embodiment, as will be explained hereinafter with reference to FIGS. 5B-5C, the cavity 166 may have a sinusoidal wave-shaped cross-section such that it defines a plurality of protrusions having a first radius and a plurality of recesses having a second radius larger than the first radius. The check valve 134 may be disposed within the cavity 166 such that it is retained between the protrusions. For example, the outer diameter of the check valve 134 may be equal to or smaller than the distance between opposing protrusions. The plurality of recesses defines a fluid path around the check valve 134. The check valve 134 is retained within the fluid channel 108 between a distal wall 138 on the intermediate part 114 and a distal projection 140 on the first connector 110.

The check valve 134 includes a plurality of openings 136 extending through the check valve 134. The plurality of openings 136 is spaced apart along the longitudinal length of the check valve 134 and extends in a radial direction through at least a portion of the diameter of the check valve 134. In another embodiment, the check valve 134 may have a solid construction that is void of any openings extending therethrough.

The compressible check valve 134 is desirably an elastomeric part that is at least partially compressible in a longitudinal direction when acted upon by fluid pressure. During an injection procedure, fluid is urged under pressure through the fluid inlet line 32 (shown in FIG. 3) before entering the first connector 110. As the fluid travels through the central lumen 156 of the first connector 110, the fluid engages a proximal face 168 of the check valve 134. Initially, the proximal face 168 engages the distal end of the distal projection 140 to block the passage of fluid into the intermediate part 114. As the fluid pressure builds, the force on the proximal face 168 of the check valve 134 increases. Due to its compressible nature, the proximal face 168 is urged in the distal direction, thereby creating a gap between the proximal face 168 and the distal end of the distal projection 140. Such a gap is formed only when sufficient fluid pressure is imparted on the proximal face 168, such as, for example, during a typical injection procedure. The pressurized fluid then travels around the check valve 134 and through the bolus control device 100 to be delivered to the patient. For example, the pressurized fluid can flow through the plurality of recesses surrounding the check valve 134. After the injection procedure is completed, the resilient nature of the check valve 134 causes it to expand axially such that the proximal face 168 engages the distal end of the distal projection 140 to prevent additional fluid from flowing through the bolus control device 100. In this manner, any excess fluid is prevented from flowing through the bolus control device 100 after the bolus of pressurized fluid is delivered therethrough.

Due to the threadable connection between the first connector 110 and the sleeve 120, the initial compression of the check valve 134 between the distal wall 138 on the intermediate part 114 and a distal projection 140 on the first connector 110 can be adjusted. By adjusting the compression of the check valve 134, the crack pressure under which the proximal face 168 of the check valve 134 is compressed in a distal direction can be adjusted. In this manner, the check valve 134 can be made stiffer by compressing it in the axial direction between the distal wall 138 on the intermediate part 114 and the distal projection 140 on the first connector 110, thereby requiring a higher pressure to open a gap between the check valve 134 and the distal projection 140. Conversely, the check valve 134 can be made softer by decompressing it in the axial direction between the distal wall 138 on the intermediate part 114 and the distal projection 140 on the first connector 110, thereby requiring a lower pressure to open a gap between the check valve 134 and the distal projection 140. Stiffness of the check valve 134 can be adjusted by rotating the sleeve 120 relative to the first connector 110.

Figure 5D:
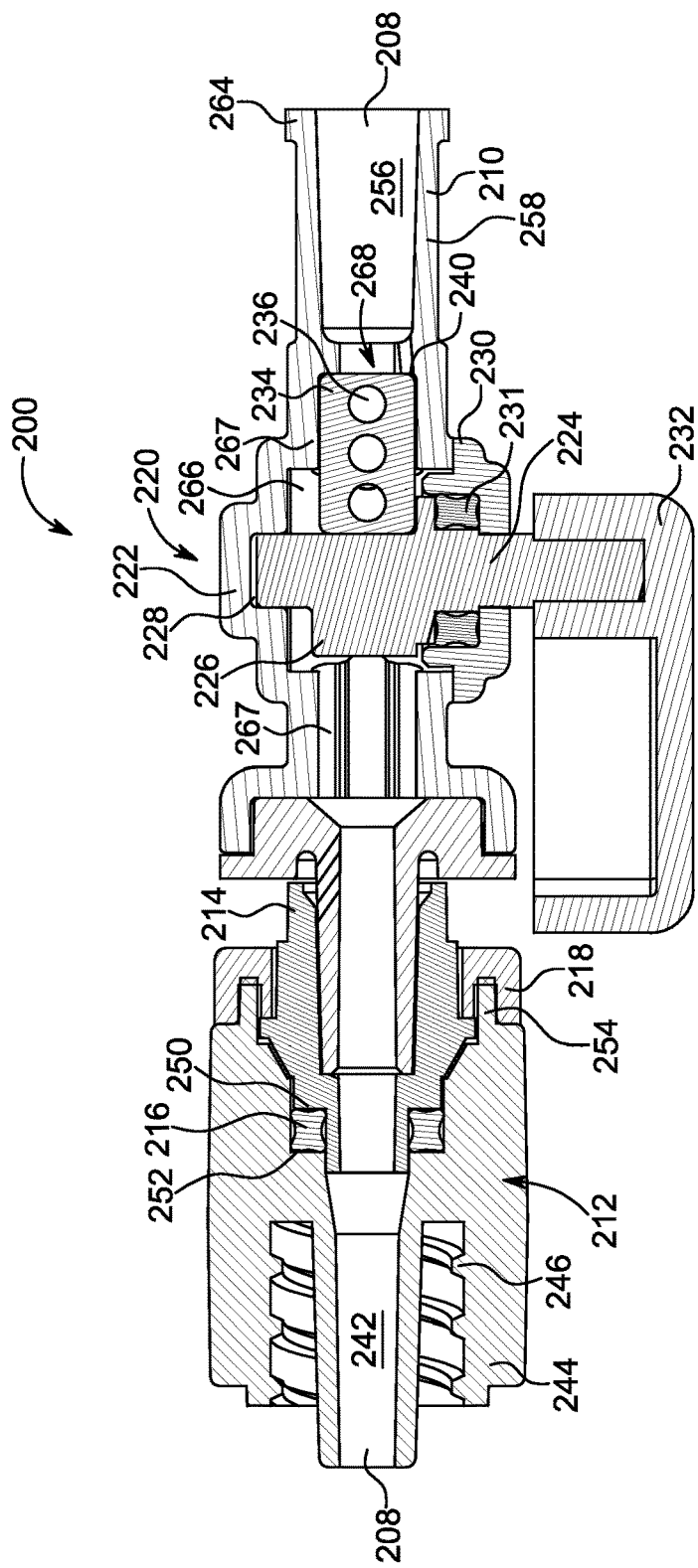
FIG. 5D is a side cross-sectional view of the bolus control device shown in FIG. 5A with an adjustment mechanism in a first position.
Figure 5E:
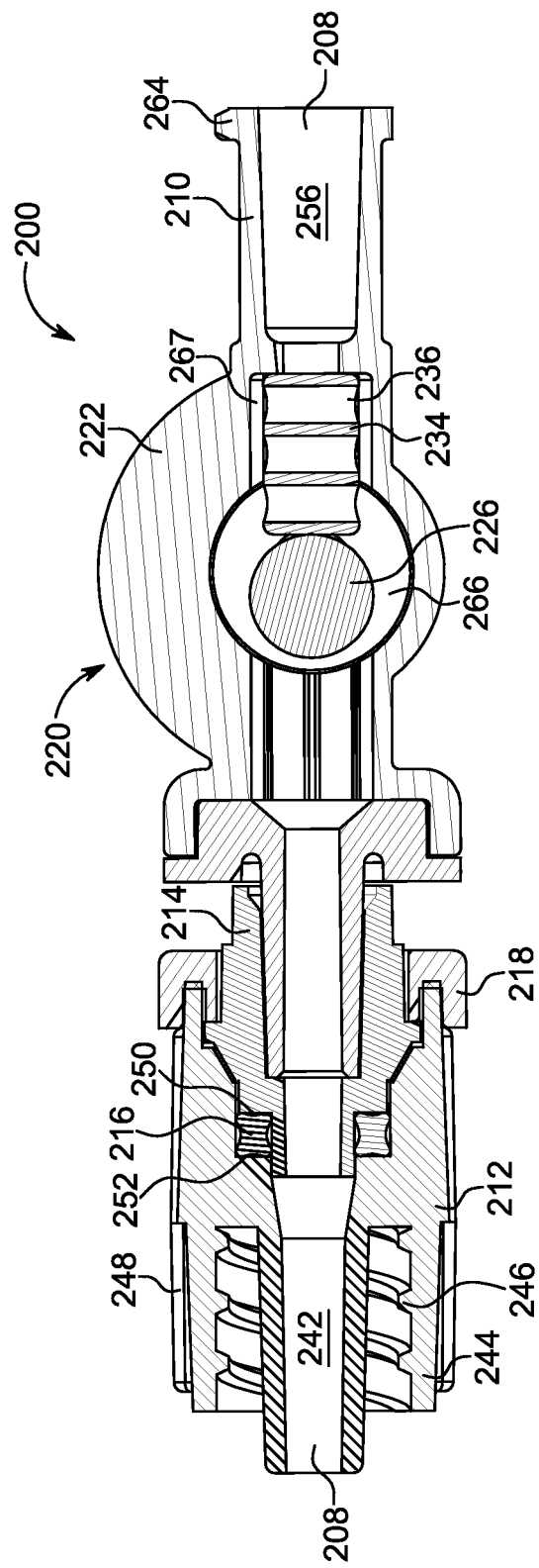
FIG. 5E is a bottom cross-sectional view of the bolus control device shown in FIG. 5A with an adjustment mechanism in a first position.
Figure 5F:
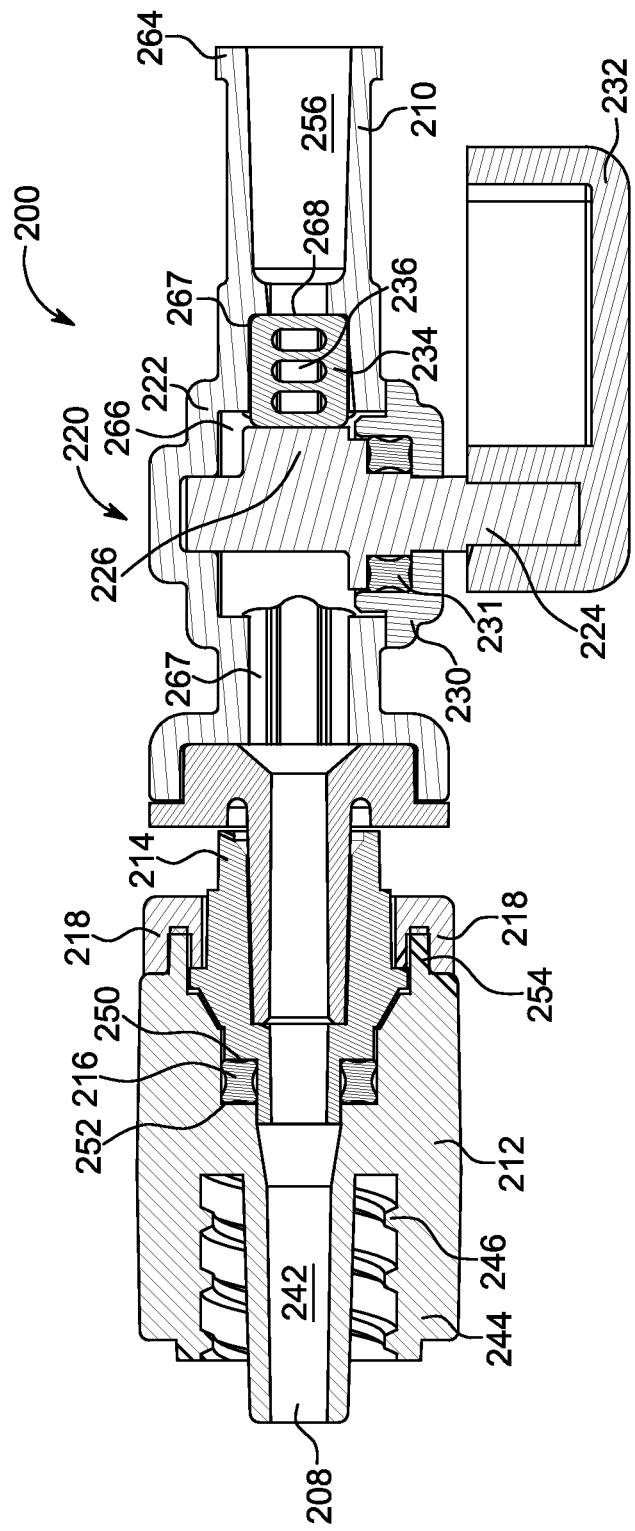
FIG. 5F is a side cross-sectional view of the bolus control device shown in FIG. 5A with an adjustment mechanism in a second position.
Figure 5G:
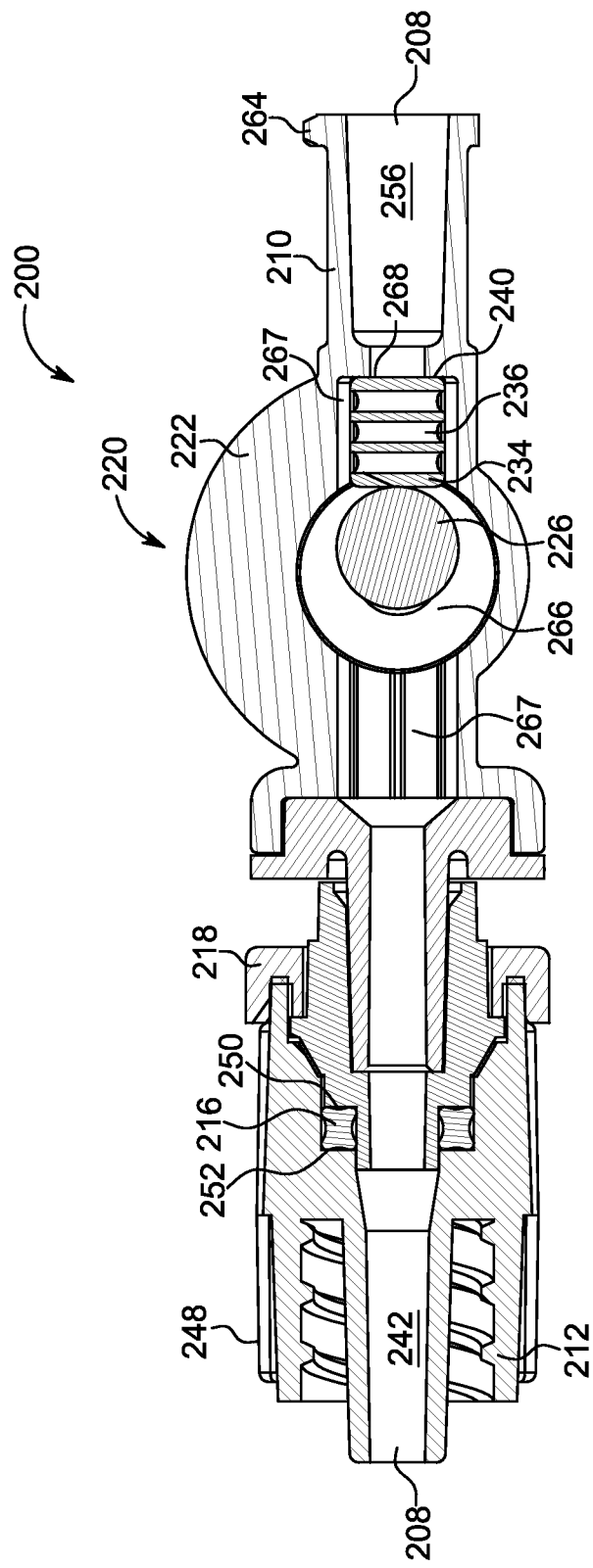
FIG. 5G is a bottom cross-sectional view of the bolus control device shown in FIG. 5A with an adjustment mechanism in a second position.
Figure 5H:
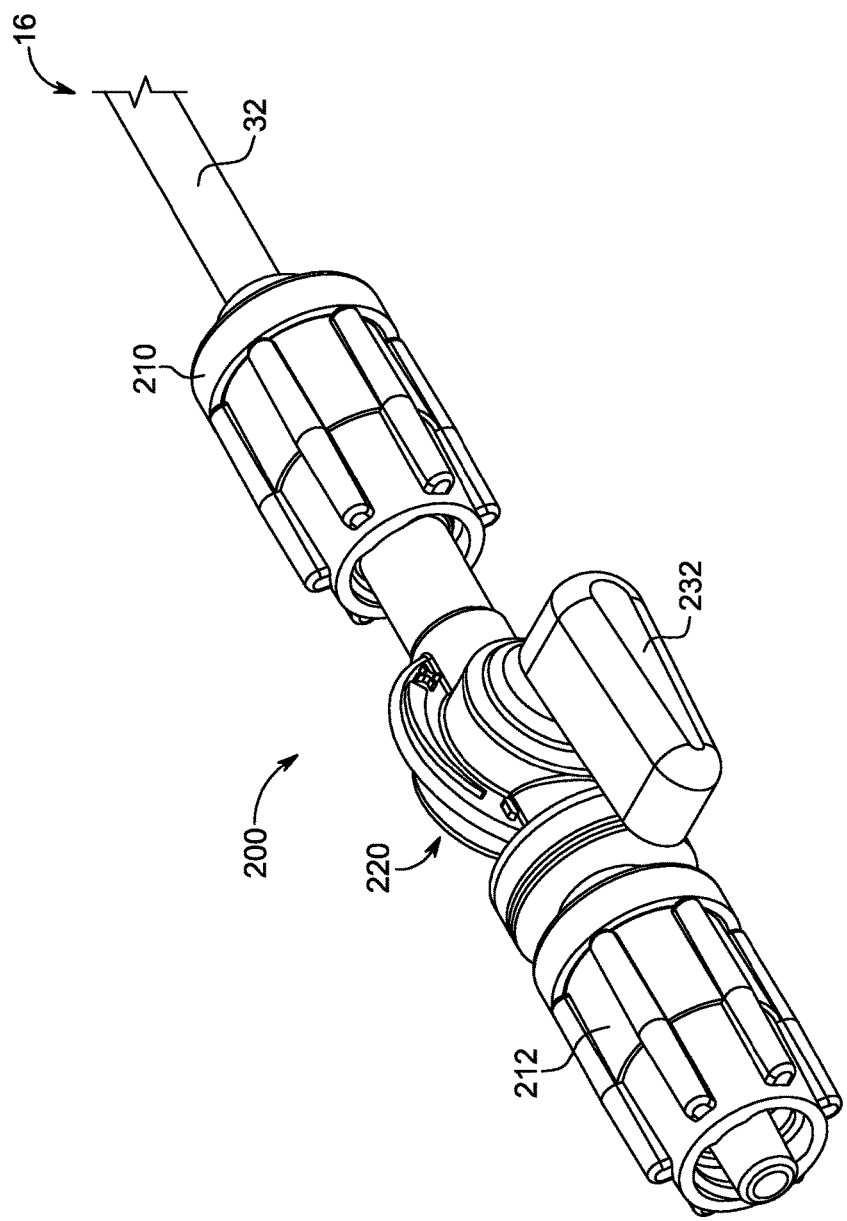
FIG. 5H is a perspective view of the bolus control device shown in FIG. 5A in connection with a fluid path set.

With reference to FIGS. 5A-5H, a bolus control device 200 is illustrated in accordance with a second embodiment. FIG. 5H illustrates the bolus control device 200 in connection with the fluid path set 16. The bolus control device 200, as described herein, is intended for connection to a fluid injection system 10 (shown in FIG. 1), as will be readily apparent to those skilled in the medical art. The bolus control device 200 includes a valve body 202 having a proximal end 204 opposite a distal end 206. The valve body 202 defines a fluid channel 208 therethrough to allow passage of fluid from the proximal end 204 to the distal end 206. A first connector 210 is provided at the proximal end 204 and is configured for connecting to a fluid inlet line (not shown). For example, the first connector 210 may be a male luer-type connector for connecting to a female end of a corresponding luer-type connector of the fluid inlet line connected to an injection device, such as a manual or automatic contrast injection mechanism. A second connector 212 is provided at the distal end 206 and is configured for connecting to a fluid outlet line, such as a catheter (not shown). Similar to the first connector 210, the second connector 212 may be a female luer-type connector for connecting to a male end of a corresponding luer-type connector of the fluid outlet line leading to an injection site. Alternatively, the first connector 210 may be a female luer-type connector, and the second connector 212 may be a male luer-type connector. In yet another embodiment, both the first and second connectors 210, 212 may be male or female luer-type connectors. One of ordinary skill in the art will appreciate that the first connector 210 and the second connector 212 may be embodied as any type of a mechanical connector known in the medical arts for connecting a plurality of components in a fluid path set 16 (shown in FIG. 5H).

With reference to FIGS. 5D-5G, the second connector 212 has a generally tubular structure with the fluid channel 208 extending along its central axis. The second connector 212 has a central lumen 242 extending along the central axis. The central lumen 242 is surrounded by an annular skirt 244 that is concentric about the central lumen 242. The annular skirt 244 has internal threads 246 configured for connecting to the fluid outlet line 36 (shown in FIG. 3). Alternatively, the annular skirt 244 may have external threads. The exterior portion of the second connector 212 has one or more protrusions 248 that extend radially outward. The protrusions 248 are configured for facilitating the handling of the bolus control device 200. For example, the protrusions 248 may provide a gripping surface that is grasped by the user to facilitate connection with the fluid outlet line 36.

With continuing reference to FIGS. 5D-5G, the second connector 212 is connected to an intermediate part 214. In one embodiment, the second connector 212 may be formed as a separate component removably or non-removably coupled with the intermediate part 214. Alternatively, the second connector 212 may be integrally formed with the intermediate part 214. The intermediate part 214 has a generally tubular structure with a distal end having a radial face 250 configured for defining a sealing interface with an annular end wall 252 on the second connector 212. A gasket 216 is disposed between the radial face 250 of the intermediate part 214 and the annular end wall 252 of the second connector 212. The gasket 216 is desirably made from a flexible and resilient material, such as rubber, to provide a seal at the interface between the second connector 212 and the intermediate part 214.

With continuing reference to FIGS. 5D-5G, a ring 218 connects the second connector 212 and the intermediate part 214 together. The ring 218 is substantially annularly shaped and defines a connection member 254 for connecting the second connector 212 to the intermediate part 214. In one embodiment, the ring 218 non-removably connects the second connector 212 and the intermediate part 214. In another embodiment, the second connector 212 and the intermediate part 214 are removably connected together. For example, the ring 218 may be threadably connected to the second connector 212 by way of the connection member 254 such that, when fully threaded with the second connector 212, the ring 218 urges the intermediate part 214 toward the second connector 212. In this manner, the gasket 216 is compressed between the second connector 212 and the intermediate part 214 to provide a sealed interface therebetween.

With particular reference to FIG. 5D, the bolus control device 200 includes an adjustment mechanism 220 for adjustably controlling a check valve 234 to prevent any dribbling of excess fluid that may be stored in the injection system (not shown) due to system capacitance. The adjustment mechanism 220 is disposed between the ring 218 and the first connector 210. The adjustment mechanism 220 includes a housing 222 with a cavity 266 adapted to receive a valve stem 224 having a cam element 226. The valve stem 224 and the cam element 226 are received within the cavity 266 in a direction substantially perpendicular to the direction of fluid flow through the bolus control device 200. One end of the valve stem 224 is received inside a recess 228 (shown in FIGS. 5D and 5F) on the housing 222, while the opposing end of the valve stem 224 extends through an opening on a valve cap 230. A seal 231 may be provided at the interface between the valve stem 224 and the valve cap 230. In another embodiment, the valve stem 224 may be secured between the recess 228 and a portion of the housing 222. A valve handle 232 is connected to the valve stem 224 such that rotation of the valve handle 232 causes a rotation of the valve stem 224 within the cavity 266. As the valve stem 224 rotates about its longitudinal axis, the cam element 226 traces an eccentric path relative to the rotation of the valve stem 224. In one embodiment, the handle 232 may be provided directly on the housing 222 of the adjustment mechanism 220 to rotate the valve stem 224 and thereby adjust the compression of the compressible check valve. In one embodiment, the handle 232 is rotatable through 180 degrees of rotation from a first position aligned with a proximal end of the housing 222 to a second position aligned with a distal end of the housing 222. A stop member (not shown) may be provided to limit the rotational movement of the handle 232 or the valve stem 224. The housing 222 may include indicia 270 (shown in FIGS. 5B-5C) that indicate the "stiffness" of a compressible check valve based on the position of the handle 232. For example, the indicia 270 may be in the form of a graduated scale corresponding to a cracking pressure of the compressible check valve.

Similar to the second connector 212, the first connector 210 has a generally tubular structure with the fluid channel 208 extending along its central axis. The first connector 210 has a central lumen 256 defined by annular skirt 258. The proximal end of the central lumen 256 has a luer-type connection 264 for connecting with the fluid inlet line 32 (shown in FIG. 5H).

With continuing reference to FIG. 5D, a compressible check valve 234 is disposed within a channel 267 between the cavity 266 of the housing 222 and the first connector 210. The channel 267 is aligned with a central axis of the bolus control device 200 such that the channel 267 defines the portion of the fluid channel 208 extending through the bolus control device 200. The compressible check valve 234 is desirably dimensioned such that its outer diameter is slightly smaller than an inner diameter of the channel 267 such that fluid passes around the check valve 234 and into the cavity 266. The check valve 234 is retained within the channel 267 between a distal projection 240 on the first connector 210 and the cam element 226. In one embodiment, shown in FIGS. 5B-5C, the channel 267 may have a sinusoidal wave-shaped cross-section such that it defines a plurality of protrusions having a first radius and a plurality of recesses having a second radius larger than the first radius. The check valve 234 may be disposed within the channel 267 such that it is retained between the protrusions. For example, the outer diameter of the check valve 234 may be equal to or smaller than the distance between opposing protrusions. The plurality of recesses define a fluid path around the check valve 234.

The check valve 234 includes a plurality of openings 236 extending through the check valve 234. The plurality of openings 236 is spaced apart along the longitudinal length of the check valve 234 and extends in a radial direction through at least a portion of the diameter of the check valve 234. In another embodiment, the check valve 234 may have a solid construction that is void of any openings extending therethrough.

The compressible check valve 234 is desirably an elastomeric part that is at least partially compressible in a longitudinal direction when acted upon by fluid pressure. During an injection procedure, fluid is urged under pressure through the fluid inlet line 32 (shown in FIG. 5H) before entering the first connector 210. As the fluid travels through the central lumen 256 of the first connector 210, the fluid engages a proximal face 268 of the check valve 234. Initially, the proximal face 268 engages the distal end of the distal projection 240 to block the passage of fluid into the intermediate part 214. As the fluid pressure builds, the force on the proximal face 268 of the check valve 234 increases. Due to its compressible nature, the proximal face 268 is urged in the distal direction, thereby creating a gap between the proximal face 268 and the distal end of the distal projection 240. Such a gap is formed only when a sufficient fluid pressure is imparted on the proximal face 268, such as, for example, during a typical injection procedure. The pressurized fluid then travels around the check valve 234 and through the bolus control device 200 to be delivered to the patient. For example, the pressurized fluid can flow through the plurality of recesses surrounding the check valve 234. After the injection procedure is completed, the resilient nature of the check valve 234 causes it to expand axially such that the proximal face 268 engages the distal end of the distal projection 240 to prevent additional fluid from flowing through the bolus control device 200. In this manner, any excess fluid is prevented from flowing through the bolus control device 200 after the bolus of pressurized fluid is delivered therethrough.

Due to the eccentric movement of the cam element 226, the initial compression of the check valve 234 between the cam element 226 and the distal projection 240 on the first connector 210 can be adjusted. By adjusting the compression of the check valve 234, the crack pressure under which the proximal face 268 of the check valve 234 is compressed in a distal direction can be adjusted. In this manner, the check valve 234 can be made stiffer by compressing it in the axial direction between the cam element 226 and the distal projection 240 on the first connector 210, thereby requiring a higher pressure to open a gap between the check valve 234 and the distal projection 240. Conversely, the check valve 234 can be made softer by decompressing it in the axial direction between the distal projection 240 on the intermediate part 214 and the distal projection 240 on the first connector 210, thereby requiring a lower pressure to open a gap between the check valve 234 and the distal projection 240.

With reference to FIGS. 5D-5E, the adjustment mechanism 220 of the bolus control device 200 is shown in a first position where the compressible check valve 234 is adjusted to a maximum compression setting where the cam element 226 is positioned in a location closest to the first connector 210. The compression of the compressible check valve 234 can be reduced by turning the valve stem 224 such that the cam element 226 is positioned in a location farthest away from the first connector 210, as shown in FIGS. 5G-5H. In this position, the compressible check valve 234 is compressed less relative to the position shown in FIGS. 5D-5E.

Adjustment of compression of the compressible check valve 234 is desirable to regulate the crack pressure for different system variables, including the procedure type, the type of the fluid path set, catheter size, the type of injection fluid, and pressure parameters.

Figure 6A:
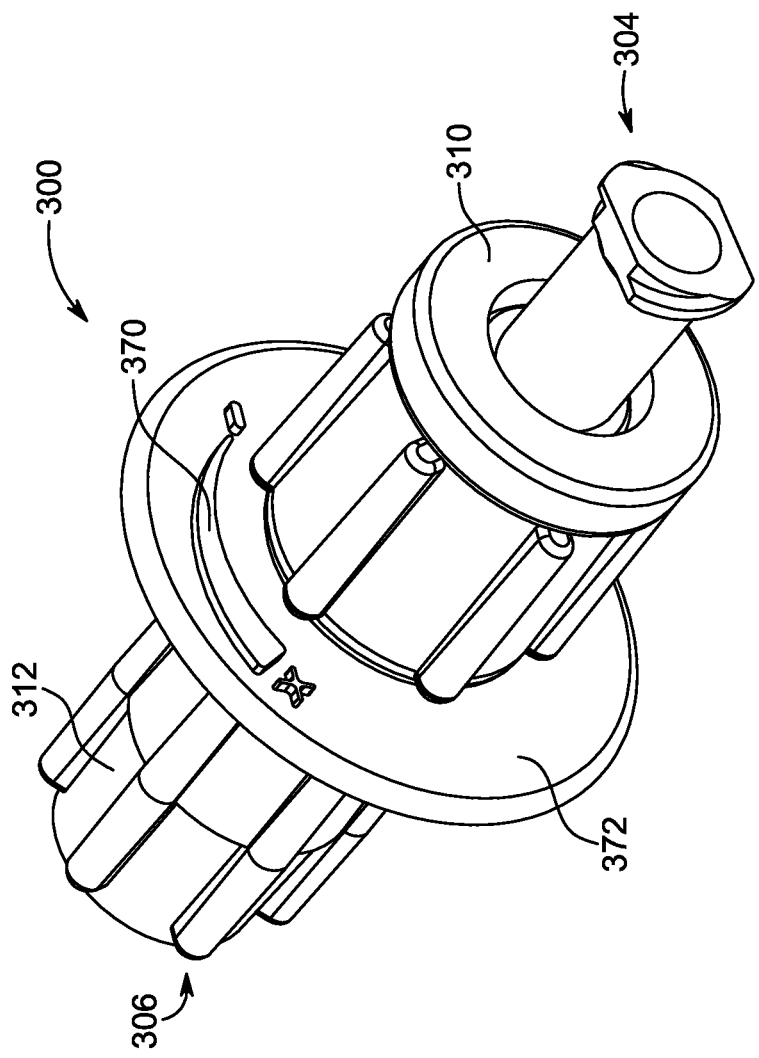
FIG. 6A is a perspective view of a bolus control device in accordance with a third embodiment.
Figure 6B:
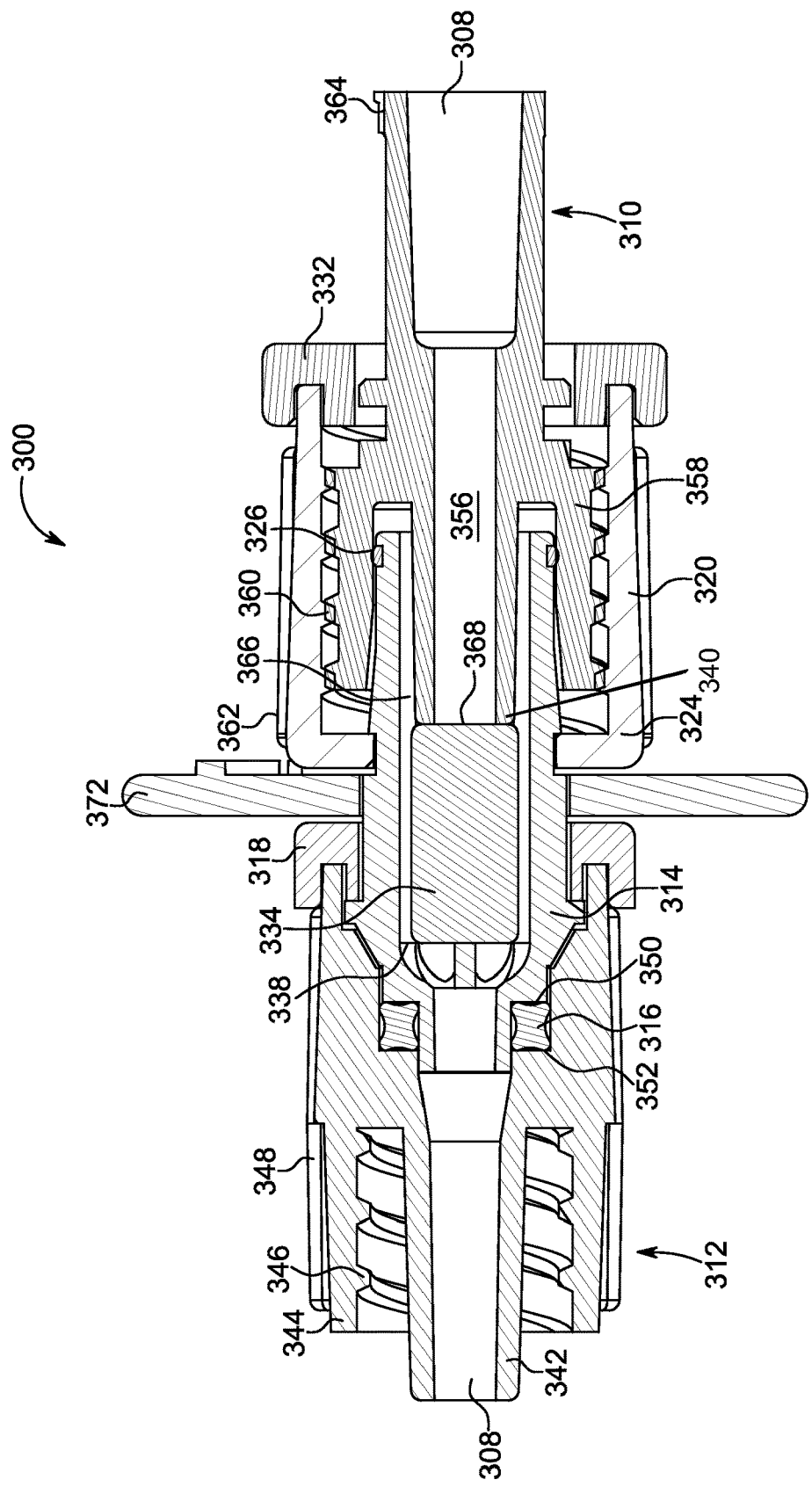
FIG. 6B is cross-sectional view of the bolus control device shown in FIG. 6A.
Figure 6C:
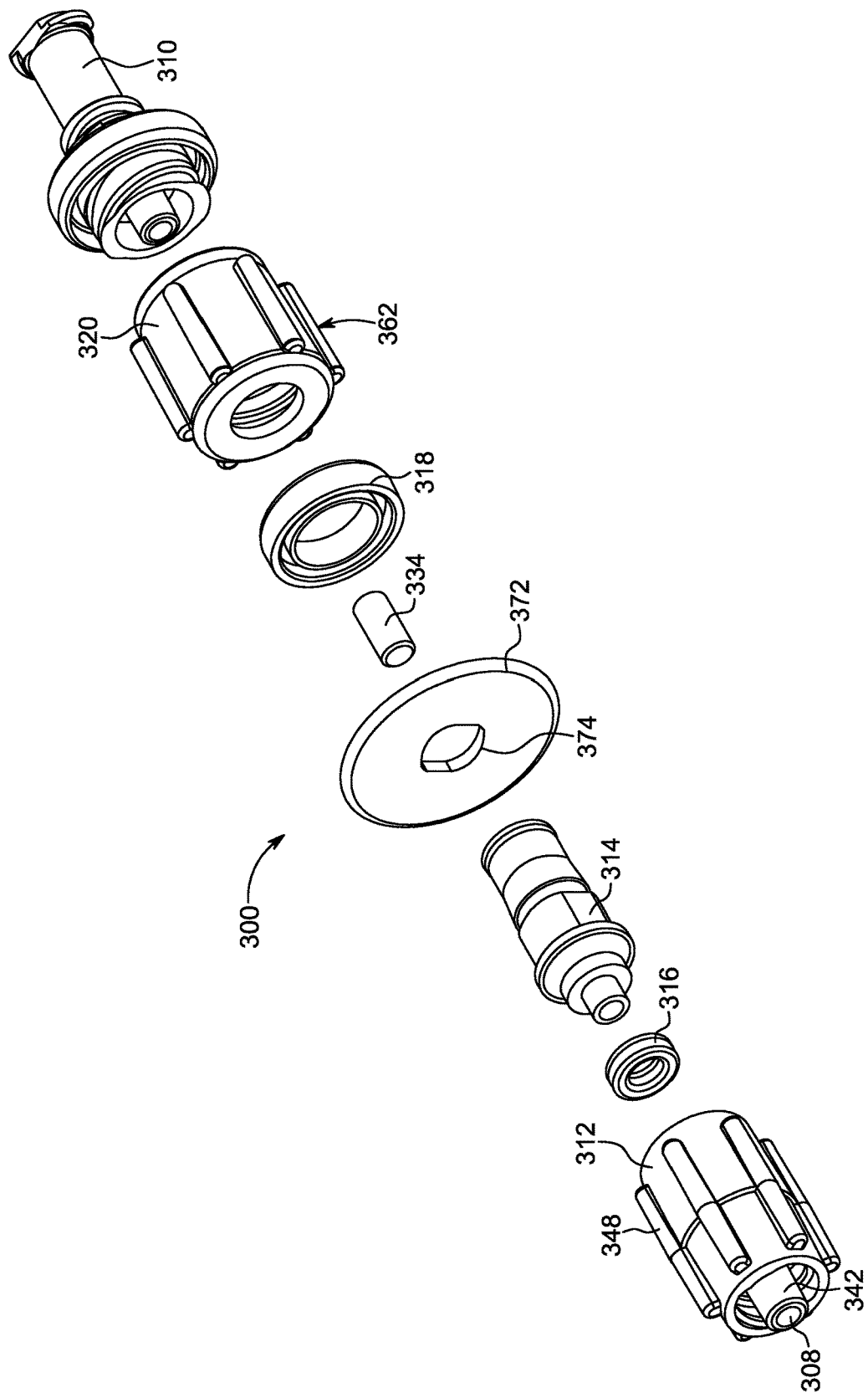
FIG. 6C is an exploded view of the bolus control device shown in FIG. 6A.

With reference to FIGS. 6A-6C, a bolus control device 300 is shown in accordance with a third embodiment. The bolus control device 300, as described herein, is intended for connection to a fluid injection system 10 (shown in FIG. 1), as will be readily apparent to those skilled in the medical art. The bolus control device 300 similar to the bolus control device 100 described hereinabove with reference to FIGS. 4A-4C. Reference numerals 302-368 in FIGS. 6A-6C are used to designate identical components as reference numerals 102-168 in FIGS. 4A-4C. Only the relative differences between the two embodiments will be discussed hereinafter.

Whereas the stiffness of the check valve 134 in FIGS. 4A-4C can be adjusted by rotating the sleeve 120 relative to the first connector 110, the bolus control device 300 in FIGS. 6A-6C includes an adjustment ring 372 disposed between the ring 318 and the sleeve 320. The adjustment ring 372 has an annular shape with a central opening 374 configured for engaging the intermediate part 314. The central opening 374 is desirably non-circular such that the adjustment ring 372 is not rotatable relative to the intermediate part 314. In one embodiment, the adjustment ring 372 may have a circular central opening 374 that is frictionally engaged with the intermediate part 314 such that the adjustment ring 372 is not rotatable relative to the intermediate part 314. The adjustment ring 372 has indicia 370 that indicate the "stiffness" of a compressible check valve 334 based on the position of the handle 332. For example, the indicia 370 may be in the form of a graduated scale corresponding to a cracking pressure of the compressible check valve 334. 8

Rotation of the adjustment ring 372 causes a corresponding rotation of the intermediate part 314, which causes the first connector 310 to rotate relative to the sleeve 320. Due to the threadable connection between the first connector 310 and the sleeve 320, the initial compression of the check valve 334 between the distal wall 338 on the intermediate part 314 and a distal projection 340 on the first connector 310 can be adjusted. By adjusting the compression of the check valve 334, the crack pressure under which the proximal face 368 of the check valve 334 is compressed in a distal direction can be adjusted. In this manner, the check valve 334 can be made stiffer by compressing it in the axial direction between the distal wall 338 on the intermediate part 314 and a distal projection 340 on the first connector 310, thereby requiring a higher pressure to open a gap between the check valve 334 and the distal projection 340. Conversely, the check valve 334 can be made softer by decompressing it in the axial direction between the distal wall 338 on the intermediate part 314 and a distal projection 340 on the first connector 310, thereby requiring a lower pressure to open a gap between the check valve 334 and the distal projection 340.

While various embodiments of the fluid path set bolus control device were provided in the foregoing description, those skilled in the art may make modifications and alterations to these embodiments without departing from the scope and spirit of the disclosure. For example, it is to be understood that this disclosure contemplates that, to the extent possible, one or more features of any embodiment can be combined with one or more features of any other embodiment. Accordingly, the foregoing description is intended to be illustrative rather than restrictive.

What is claimed is:

1. A bolus control device for use with an injection device, the bolus control device comprising:
    a valve body having a proximal end opposite a distal end, the valve body defining a fluid channel therethrough;
    a first connector at the proximal end configured for connecting to a fluid inlet line;
    a second connector at the distal end configured for connecting to a fluid outlet line;
    a compressible check valve disposed within the fluid channel between the proximal end of the valve body and the distal end of the valve body, the compressible check valve having a body made from a reversibly compressible material and a closed proximal end, a distal end, and a plurality of transverse openings extending through the compressible check valve body between the closed proximal end of the compressible check valve body and the distal end of the compressible check valve body, wherein the compressible check valve body is compressible longitudinally between the proximal end of the valve body and the distal end of the valve body in response to fluid pressure within the fluid channel; and
    an adjustment mechanism configured to adjust an axial position of the first connector relative to the distal end of the compressible check valve body, wherein adjustment of the axial position of the first connector varies a compression of the compressible check valve, and
    wherein the reversibly compressible material of the compressible check valve is reversibly compresses with movement of the adjustment mechanism to increase or decrease a cracking pressure at which the compressible check valve opens to allow fluid flow around the compressible check valve body and through the fluid channel during a pressurized delivery of fluid through the valve body.

2. The bolus control device of claim 1, further comprising an intermediate element disposed between the first connector and the second connector, wherein the fluid channel extends through an interior cavity of the intermediate element.

3. The bolus control device of claim 2, wherein the compressible check valve is disposed within the interior cavity of the intermediate element and wherein the fluid channel extends radially around the compressible check valve.

4. The bolus control device of claim 2, wherein the compressible check valve is disposed between a distal end of the first connector and a distal end of the intermediate element and wherein the compressible check valve is compressible under fluid pressure in a distal direction from the distal end of the first connector toward the distal end of the intermediate element.

5. The bolus control device of claim 2, wherein the adjustment mechanism comprises a sleeve extending around at least a portion of the first connector and at least a portion of the intermediate element, wherein the sleeve is rotatable relative to the first connector to adjust the axial position of the first connector relative to the intermediate element.

6. The bolus control device of claim 5, wherein the sleeve is connected to the first connector by a threaded connection.

7. The bolus control device of claim 5, wherein rotation of the sleeve relative to the first connector adjusts the compression of the compressible check valve.

8. A fluid path set for use with an injection device, the fluid path set comprising:
   a fluid inlet line;
   a fluid outlet line; and
   a bolus control device disposed between the fluid inlet line and the fluid outlet line, the bolus control device comprising:
      a valve body having a proximal end opposite a distal end, the valve body defining a fluid channel therethrough;
      a first connector at the proximal end in fluid connection with the fluid inlet line;
      a second connector at the distal end in fluid connection with the fluid outlet line;
      a compressible check valve disposed within the fluid channel between the proximal end and the distal end of the valve body, the compressible check valve having a body made from a reversibly compressible material and a closed proximal end, a distal end, and a plurality of transverse openings extending through the compressible check valve body between the closed proximal end of the compressible check valve body and the distal end of the compressible check valve body; and
      an adjustment mechanism configured to adjust an axial position of the first connector relative to the distal end of the compressible check valve body, wherein adjustment of the axial position of the first connector varies a compression of the compressible check valve,
      wherein the reversibly compressible material of the compressible check valve is reversibly compresses longitudinally between the proximal end of the valve body and the distal end of the valve body in response to fluid pressure within the fluid channel, and
      wherein movement of the adjustment mechanism increases or decreases a compression of the reversibly compressible material to increase or decrease a cracking pressure at which the compressible check valve opens to allow fluid flow around the compressible check valve body and through the fluid channel during a pressurized delivery of fluid through the valve body.

9. The fluid path set of claim 8, further comprising an intermediate element disposed between the first connector and the second connector, wherein the fluid channel extends through an interior cavity of the intermediate element.

10. The fluid path set of claim 8, wherein the first connector is connected to the fluid inlet line by a threaded connection.

11. The fluid path set of claim 8, wherein the second connector is connected to the fluid outlet line by a threaded connection.

12. The fluid path set of claim 8, wherein the fluid inlet line is configured for connecting to the injection device.

13. The fluid path set of claim 8, wherein the fluid outlet line is configured for connecting to a catheter for delivering fluid to a patient.

14. A bolus control device for use with an injection device, the bolus control device comprising:
   a valve body having a proximal end opposite a distal end, the valve body defining a fluid channel therethrough;
   a first connector at the proximal end configured for connecting to a fluid inlet line;
   a second connector at the distal end configured for connecting to a fluid outlet line;
   a compressible check valve disposed within the fluid channel between the proximal end of the valve body and the distal end of the valve body, the compressible check valve having a body made from a reversibly compressible material and a closed proximal end, a distal end, and a plurality of transverse openings extending through the compressible check valve body between the closed proximal end of the compressible check valve body and the distal end of the compressible check valve body; and
   an adjustment mechanism for varying a compression of the compressible check valve against the first connector, wherein the adjustment mechanism comprises an eccentric cam element and a rotatable valve stem associated with the distal end of the compressible check valve body,
   wherein the reversibly compressible material of the compressible check valve is reversibly compresses longitudinally between the proximal end of the valve body and the distal end of the valve body in response to fluid pressure within the fluid channel, and
   wherein movement of the adjustment mechanism increases or decreases a compression of the reversibly compressible material to increase or decrease a cracking pressure at which the compressible check valve opens to allow fluid flow around the compressible check valve body and through the fluid channel during a pressurized delivery of fluid through the valve body.

15. The bolus control device of claim 14, wherein the adjustment mechanism includes a housing with a cavity configured to receive the rotatable valve stem and the eccentric cam element.

16. The bolus control device of claim 15, wherein the compressible check valve is disposed between a distal end of the first connector and the eccentric cam element and wherein the compressible check valve is compressible under fluid pressure in a distal direction from the distal end of the first connector toward the eccentric cam element.

17. The bolus control device of claim 15, wherein the eccentric cam element and the rotatable valve stem are rotatable within the housing of the adjustment mechanism.

18. The bolus control device of claim 17, wherein rotation of the eccentric cam element and the rotatable valve stem adjusts the compression of the compressible check valve against the first connector to control the cracking pressure at which the compressible check valve opens to allow fluid flow through the fluid channel.

19. The bolus control device of claim 14, further comprising an intermediate element disposed between the second connector and the housing of the adjustment mechanism, wherein the fluid channel extends through an interior cavity of the intermediate element.

* * * * *

UNITED STATES PATENT AND TRADEMARK OFFICE
CERTIFICATE OF CORRECTION

PATENT NO. : 10,441,775 B2
APPLICATION NO. : 14/888298
DATED : October 15, 2019
INVENTOR(S) : Schriver et al.

Page 1 of 1

It is certified that error appears in the above-identified patent and that said Letters Patent is hereby corrected as shown below:

In the Specification

In Column 15, Line 35, delete "334. 8" and insert -- 334. --, therefor.

In the Claims

In Column 16, Line 34, in Claim 1, delete "valve is reversibly" and insert -- valve body reversibly --, therefor.
In Column 17, Line 35, in Claim 8, delete "valve is reversibly" and insert -- valve body reversibly --, therefor.
In Column 18, Line 26, in Claim 14, delete "valve is reversibly" and insert -- valve body reversibly --, therefor.

Signed and Sealed this
Fourteenth Day of January, 2020

Andrei Iancu
*Director of the United States Patent and Trademark Office*